United States Patent
Duong et al.

(10) Patent No.: US 11,117,860 B2
(45) Date of Patent: Sep. 14, 2021

(54) PHENYL UREA DERIVATIVES AS N-FORMYL PEPTIDE RECEPTOR MODULATORS

(71) Applicant: Allergan, Inc., Irvine, CA (US)

(72) Inventors: Tien T. Duong, Rancho Santa Margarita, CA (US); Richard L. Beard, Newport Beach, CA (US); Michael E. Garst, Newport Beach, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 16/090,068

(22) PCT Filed: Mar. 28, 2017

(86) PCT No.: PCT/US2017/024531
§ 371 (c)(1),
(2) Date: Sep. 28, 2018

(87) PCT Pub. No.: WO2017/172761
PCT Pub. Date: Oct. 5, 2017

(65) Prior Publication Data
US 2019/0127319 A1 May 2, 2019

Related U.S. Application Data

(60) Provisional application No. 62/314,108, filed on Mar. 28, 2016.

(51) Int. Cl.
*C07C 275/30* (2006.01)
*A61P 29/00* (2006.01)

(52) U.S. Cl.
CPC ............ *C07C 275/30* (2013.01); *A61P 29/00* (2018.01)

(58) Field of Classification Search
CPC .............................. C07C 275/30; A61P 29/00
See application file for complete search history.

(56) References Cited

U.S. PATENT DOCUMENTS

| | | | |
|---|---|---|---|
| 6,387,383 B1 | 5/2002 | Dow | |
| 6,468,989 B1 | 10/2002 | Chang | |
| 6,517,847 B2 | 2/2003 | Dow | |
| 2003/0191279 A1 | 10/2003 | Goldstein et al. | |
| 2009/0105231 A1 | 4/2009 | Sawada et al. | |
| 2013/0109866 A1 | 5/2013 | Beard et al. | |
| 2013/0123496 A1 | 5/2013 | Beard et al. | |
| 2014/0256684 A1 | 9/2014 | Beard | |

FOREIGN PATENT DOCUMENTS

| | | |
|---|---|---|
| WO | 03042204 | 5/2003 |
| WO | 2014138037 | 9/2014 |
| WO | 2014138046 | 9/2014 |
| WO | 2017023907 | 2/2017 |

OTHER PUBLICATIONS

STN Registry entry for CAS RN 1384611-66-8, Entered STN Jul. 27, 2012, Accessed Jul. 23, 2019.*
STN Registry database entry for CAS RN 1322301-99-4, entry date of Aug. 24, 2011, Accessed Apr. 13, 2020.*
Ito et al. in Cancer Science 94(1), 3-8 (2003).*
Alam, A. et al., Redox signaling regulates commensal-mediated mucosal homeostasis and restitution and requires formyl peptide receptor 1, Mucosal Immunology, May 2014, pp. 645-655, vol. 7, No. 3.
Babbin, B.A., Annexin A1 Regulates Intestinal Mucosal Injury, Inflammation, and Repair, The Journal of Immunology, 2008, pp. 5035-5044, 181.
Chiang, Nan, et al., The Lipoxin Receptor ALX: Potent Ligand-Specific and Stereoselective Actions in Vivo, Pharmacological Reviews, 2006, 463-487, 58, No. 3.
Gennaro, Alfonso, Remington: The Science and Practice of Pharmacy, 1995, 1517-1518, 2.
Giebeler, Arne et al., Deficiency of Formyl Peptide Receptor 1 and 2 Is Associated with Increased Inflammation and Enhanced Liver Injury after LPS-Stimulation, PLoS One, Jun. 2014, pp. 1-12, vol. 9, Issue 6, e100522.
International Search Report & Written Opinion dated May 22, 2017 for PCT/US2017/024531 filed on Mar. 28, 2016 in the name of Allergan, Inc.
Leoni, Giovanna, et al., Annexin A1, formyl peptide receptor, and NOX1 orchestrate ephithelial repair, The Journal of Clinical Investigation, 2013, 443-54, 123.
Liu, Mingyong et al., Formylpeptide receptors are critical for rapid neutrophil mobilization in host defense against Listeria monocytogens, Scientific Reports, 2012, pp. 1-7, vol. 2, 786.
Liu, Mingyong et al., Formylpeptide Receptors Mediate Rapid Neutrophil Mobilization to Accelerate Wound Healing, PLOS One, 2014, pp. 1-7, vol. 9, Issue 3, e90613.
Oldekamp, Sandra, Lack of formyl peptide receptor 1 and 2 leads to more severe inflammation and higher mortality in mice with of pneumococcal meningitis, Immunology, 2014, pp. 447-461, vol. 143, John Wiley & Sons Ltd.

(Continued)

*Primary Examiner* — Alicia L Otton
(74) *Attorney, Agent, or Firm* — Jonathan Bass

(57) ABSTRACT

The present disclosure relates to phenyl urea derivatives useful for the treatment of inflammatory diseases, pharmaceutical compositions containing them and their use as modulators of the N-formyl peptide receptor (FPR), including FPR1 and FPR2, or as selective agonists of the FPR1 receptor.

7 Claims, No Drawings

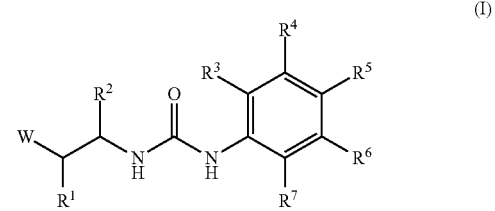

(56) References Cited

OTHER PUBLICATIONS

Schneider, Erich H., The Leukocyte Chemotactic Receptor FPR1 Is Functionally Expressed on Human Lens Epithelial Cells, The Journal of Biological Chemistry, Nov. 23, 2012, pp. 40779-40792, vol. 287, No. 48.
Tsai, et al., Formyl peptide receptor modulators: a patent review and potential applications for inflammatory: disease, Expert Opinion on Therapeutic Patents, 2016, 1-18, 26 (10).
Whiting, et al., Rapid Discovery and Structure-Activity Profiling of Novel Inhibitors of Human Immunodeficiency Virus Type 1 Protease Enabled by the Copper(I)-Catalyzed Synthesis of 1,2,3-Triazoles and Their Further Functionalization, J. Med. Chem., 2006, 7697-7710, 49.
Gennaro, Alfonso, Remington: The Science and Practice of Pharmacy, 1995, 282-291, 1.
Cross et al., Rules for the Nomenclature of Organic Chemistry, Pure & Appli. Chern, 1976,11-30, vol. 45.
Dufton, N., et al., Therapeutic anti-inflammatory potential offormyl-peptide receptor agonists, Pharmacology & Therapeutics, 2010, 175-188, 127.
Stahl, P., et al., Handbook of Pharmaceutical Salts, Properties, Selection, and Use, 2002, 329-345.

\* cited by examiner

PHENYL UREA DERIVATIVES AS N-FORMYL PEPTIDE RECEPTOR MODULATORS

CROSS-REFERENCE TO RELATED APPLICATIONS

This application is a national stage entry under 35 USC 371 of International Application PCT/US2017/024531, filed Mar. 28, 2017, which claims priority to U.S. Provisional Patent Application No. 62/314,108 filed on Mar. 28, 2016, the entire contents of which are incorporated herein by this specific reference.

FIELD OF THE INVENTION

The present invention relates to phenyl urea derivatives, processes for preparing them, pharmaceutical compositions containing them and their use as pharmaceuticals as modulators of N-formyl peptide receptor(s) (FPR(s)), such as modulators of the N-formyl peptide receptor 1 (FPR1) and the N-formyl peptide receptor 2 (FPR2; also known as FPRL-1 or ALXA4), or as selective modulators of FPR1 relative to FPR2. The invention relates specifically to the use of these compounds and their pharmaceutical compositions to treat disorders associated with FPR modulation, such as FPR1 and FPR2 agonism, FPR1 agonism, or selective agonism of FPR1 relative to FPR2.

BACKGROUND OF THE INVENTION

The FPR family belongs to the seven transmembrane domain chemoattractant G-protein-coupled receptor (GPCR) family. There are three members of this family in humans: FPR1, FPR2 and FPR3. FPRs are critical regulators of host defense in phagocytosis, and are considered highly relevant factors for the chemotaxis of immune cells. These receptors represent an important pro-resolutionary molecular target for the development of new therapeutic agents in diseases or conditions involving excessive inflammatory responses. A review of FPR patent literature was published by Tsai et al. in 2016 (Tsai Y-F, Yang S-C, Hwang T-L, Formyl peptide receptor modulators: a patent review and potential applications for inflammatory disease (2012-2015), *Expert Opinion on Therapeutic Patents*, pp. 1-18, 2016).

FPR2 is expressed predominantly on inflammatory cells, such as monocytes and neutrophils, as well as on T cells, and has been shown to play a critical role in leukocyte trafficking during inflammation and human pathology (See Chiang N, Serhan C N, Dahlen, S, Drazen J M, Hay D WP, Rovati E, Shimizu T, Yokomizo T, Brink, C, The lipoxin receptor ALX: Potent ligand-specific and stereoselective actions in vivo, *Pharmacological Reviews* 2006; 58: 463-519).

FPRs are also expressed by immune cells of the central nervous system (CNS), and FPR expression is up-regulated during bacterial meningitis. Lack of FPR1 and FPR2 leads to more severe inflammation and higher mortality in mice infected with *Streptococcus pneumonia* within the CNS, suggesting that these FPRs play an important role in the innate response against this pathogen in the CNS (Oldekamp, S. et al., *Immunology*, 143(3), pp. 447-461, 2014).

FPR1 and FPR2 mediate rapid neutrophil mobilization to accelerate wound healing, as shown in Listeria-infected mice. These FPRs sense pathogen-derived chemotactic ligands and recognize host-derived chemotactic peptides in inflammation and injury. The FPRs promote the healing of sterile skin wounds in mice by initiating neutrophil infiltration (Liu, M. et al., *PLoS One*, 9(6): e90613, 2014). FPRs were also shown to guide the first wave of neutrophil infiltration in livers of Listeria-infected mice to effectively eliminate the invading pathogen (Liu, M. et al., *Sci. Rep.*, Vol 2, pp. 786, 2012). FPR1 and FPR2 deficiency has been associated with increased inflammation and enhanced liver injury after LPS stimulation. The FPRs appear to play a prominent role in regulating the hepatic inflammatory response after LPS induced liver injury (Giebeler, A. et al., *PLoS One*, 9(6): e100522, 2014).

A complex array of proinflammatory and protective mechanisms regulates inflammation and severity during intestinal mucosal injury. Controlling inflammatory responses and promoting epithelial restitution and barrier recovery requires secretion of anti-inflammatory mediators (Babbin, B. A. et al., *J. Immunol.*, 208, 181(7), pp. 5035-5044). FPR1, a chemo-attractant receptor expressed mainly on leukocytes, is expressed in epithelia, and an FPR1/NADPH oxidase (NOX1)-dependent redox signaling pathway that promotes mucosal wound repair has been delineated in intestinal epithelia. Specific gut microbiota stimulate FPR1 on intestinal epithelial cells, generating reactive oxygen species via enterocyte NOX1, causing rapid phosphorylation of focal adhesion kinase (FAK) and extracellular signal-regulated kinase mitogen-activated protein kinase, which together stimulate migration and proliferation of enterocytes adjacent to colonic wounds. FPR1 was thus identified as a pattern recognition receptor for perceiving the enteric microbiota that promotes mucosal wound repair by generating reactive oxygen species from the enterocyte NOX1. (See Leoni, G. et al., *J. Clin. Invest.*, Vol 123, pp. 443-454, 2013; Alam, A. et al., *Mucosal Immunol.*, 2014, 7(3), pp. 645-655). Regarding FPR2, the role of the ALX/FPR2 receptor-ligand interaction in regulating dextran sulfate sodium (DDS)-induced colitis revealed that treatment with an ALX/FPR2 agonist, 15-epi-lipoxin A4, reverses the enhanced sensitivity of annexin A1 (−/−) mice to DDS-colitis (Babbin, B. A. et al., supra).

FPR1 is also functionally expressed on human lens epithelial cells and appears to have a direct functional role in lens development and maintenance (Schneider et al., *J. Biol. Chem.*, V287, pp. 40779-40792, 2012).

Whiting et al. disclose the following compound in the *Journal of Medicinal Chemistry* (2006), 49(26), pp. 7697-7710, as an inhibitor of human immunodeficiency virus type 1 protease:

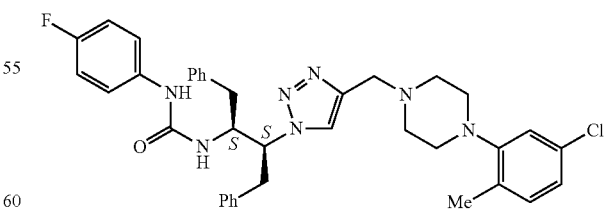

WO 03/042204 at pages 124-127 discloses [1-[3-(indol-3-yl)propanoyl]-1,2,3,4-tetrahydroquinolin-3-ylmethyl] amine derivatives as somatostatin receptor binding inhibitors, including compounds having the following structures and related compounds:

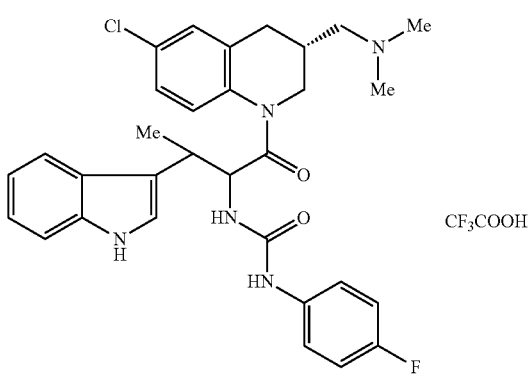

CF₃COOH

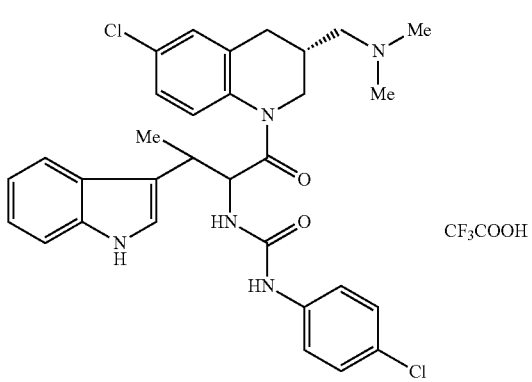

CF₃COOH

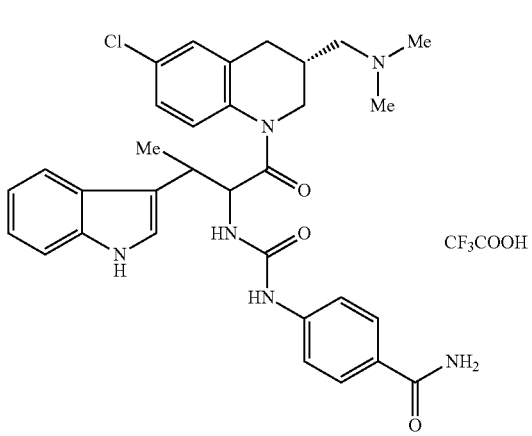

CF₃COOH

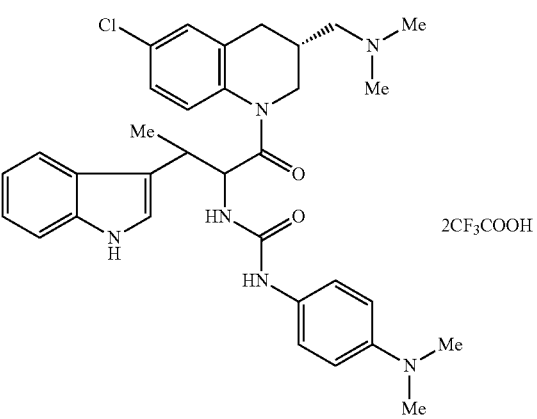

2CF₃COOH

The following are known chemical substances:

Butanoic acid, 3-[[[(4-fluoro-3-methoxyphenyl)amino]carbonyl]amino]-2-methyl—(CAS Registry No. 1770545-30-6) having the following structure:

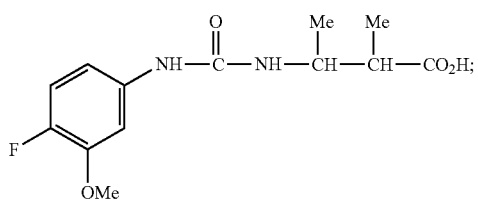 [SMILES: COc1cc(NC(=O)NC(C)C(C)C(=O)O)ccc1F]

Butanoic acid, 3-[[[(4-bromo-5-fluoro-2-methylphenyl)amino]carbonyl]amino]2-methyl—(CAS Registry No. 1770081-72-5) having the following structure:

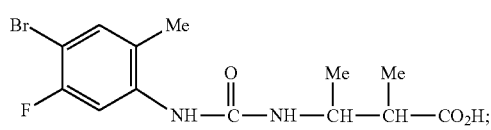

and

Urea, N-(3-chloro-4-methylphenyl)-N'[1-methyl-2-(1H-1,2,4-triazol-1-yl)propyl]—(CAS Registry No. 1333768-51-6) having the following structure:

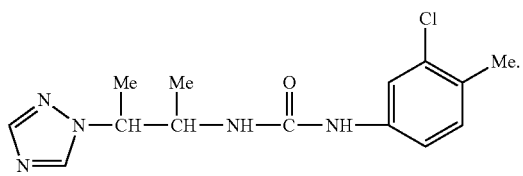 [SMILES: Cc1ccc(NC(=O)NC(C)C(C)n2cncn2)cc1Cl]

US 2013/0109866, the entire disclosure of which is incorporated herein by this specific reference, discloses compounds of the general structure below as FPR modulators for the treatment of a variety of diseases or conditions, including ocular and dermal inflammatory diseases and conditions:

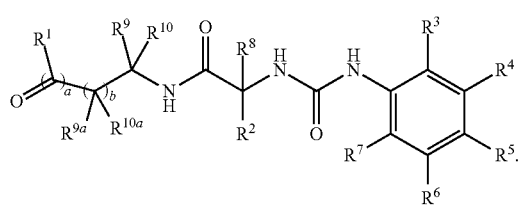

WO2017023907, the entire disclosure of which is incorporated herein by this specific reference, discloses glycine amide compounds of the general structure below, including compounds that exhibit selective agonism of the FPR1 receptor relative to the FPR2 receptor for the treatment of a variety of diseases or conditions, including ocular and dermal inflammatory diseases and conditions:

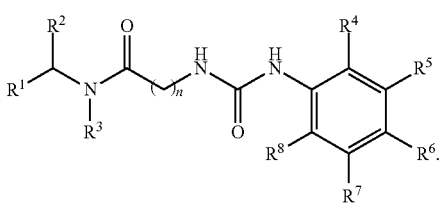

We have discovered new phenyl urea derivative compounds of the general structure of Formula I disclosed herein that exhibit selectivity for FPR1 relative to FPR2.

SUMMARY OF THE INVENTION

A group of phenyl urea derivatives, which are potent FPR modulators and which exhibit selective FPR1 modulation relative to FPR2, has been discovered. As such, the compounds described herein are useful in treating a wide variety of disorders associated with modulation of the FPR receptor, such as modulation of FPR1 and FPR2, or modulation of FPR1, or selective modulation of FPR1 relative to FPR2. The term "modulator" as used herein, includes but is not limited to: receptor agonist, antagonist, inverse agonist, inverse antagonist, partial agonist, and partial antagonist.

This invention describes compounds of Formula I, I-A, I-B, I-C and I-D, which modulate FPR biological activity. The compounds in accordance with the present invention are thus of use in medicine, for example, in the treatment of mammalian subjects, including humans, with diseases and/or conditions that are modulated or alleviated by FPR modulation, such as FPR1 and FPR2 agonism, or FPR1 agonism, or selective agonism of FPR1 relative to FPR2.

In one aspect, the invention provides a compound of Formula I:

Formula I

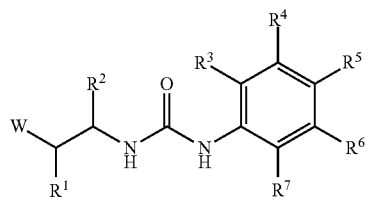

wherein:
W is —COOH, —C(O)OR$^a$, sulfonate, sulfonic acid, phosphonate, phosphonic acid, phosphoric acid, boronic acid or Het$^1$;
wherein R$^a$ is optionally substituted C$_{1-6}$ alkyl, wherein said optional substituent is selected from the group consisting of —OH, halogen, —OC$_{1-8}$ alkyl and —(CO$_{1-8}$ alkylene)$_q$-OC$_{1-8}$ alkyl, wherein q is 1, 2, 3, 4, 5 or 6; and wherein Het$^1$ is a 5-membered aromatic heterocycle optionally substituted with one or more halogen, unsubstituted —C$_{1-6}$ alkyl, —C$_{1-6}$ haloalkyl, —OC$_{1-6}$alkyl, —(CH$_2$)$_{1-6}$OH, —(CH$_2$)$_{1-6}$NH$_2$, —(CH$_2$)$_{1-6}$NH(C$_{1-6}$ alkyl) or —(CH$_2$)$_{1-6}$NR$^{14}$R$^{15}$;
R$^1$ is optionally substituted C$_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{14}$R$^{15}$, urea, —COOH, —C(O)OC$_{1-6}$ alkyl, —C(O)NH$_2$, optionally substituted C$_{3-8}$ cycloalkyl, optionally substituted C$_{3-8}$ cycloalkenyl, optionally substituted C$_{6-10}$ aryl, and optionally substituted heterocycle;
R$^2$ is optionally substituted C$_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{14}$R$^{15}$, urea, —COOH, —C(O)OC$_{1-6}$ alkyl, —C(O)NH$_2$, optionally substituted C$_{3-8}$ cycloalkyl, optionally substituted C$_{3-8}$ cycloalkenyl, optionally substituted C$_{6-10}$ aryl, and optionally substituted heterocycle;
R$^3$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^9$, —S(O)$_m$R$^{10}$, —C(O)R$^{11}$, —SR$^{12}$ or —OR$^{12}$,
R$^4$ is H, optionally substituted C$_{1-6}$ alkyl, C$_{1-6}$ haloalkyl, halogen, —S(O)$_m$R$^{10}$ or —C(O)R$^{11}$,
R$^5$ is optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —S(O)$_m$R$^{10}$, —C(O)R$^{11}$, —SR$^{13}$ or —OR$^{13}$,
R$^6$ is H, optionally substituted C$_{1-6}$ alkyl, C$_{1-6}$ haloalkyl, halogen, —S(O)$_m$R$^{10}$ or —C(O)R$^{11}$,
R$^7$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^9$, —S(O)$_m$R$^{10}$, —C(O)R$^{11}$, —SR$^{12}$ or —OR$^{12}$,
R$^8$ is H, optionally substituted C$_{1-6}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^9$ is H, optionally substituted C$_{1-6}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^{10}$ is —OH, optionally substituted C$_{1-6}$ alkyl or optionally substituted C$_{6-10}$ aryl;
R$^{11}$ is —OH, optionally substituted C$_{1-6}$ alkyl or optionally substituted C$_{6-10}$ aryl;
R$^{12}$ is H or optionally substituted C$_{1-8}$ alkyl;
R$^{13}$ is H, optionally substituted C$_{1-8}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^{14}$ is C$_{1-6}$ alkyl;
R$^{15}$ is C$_{1-6}$ alkyl; and
each m is independently 1 or 2;
or a mixture of two or more diastereomers thereof;
or a mixture of enantiomers thereof;
or an individual enantiomer or diastereoisomer thereof;
or a pharmaceutically acceptable salt of any of the foregoing;
provided that the compound is not:

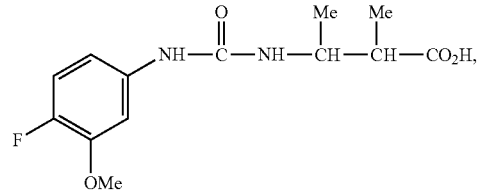

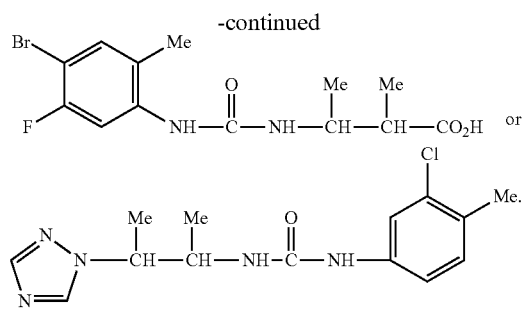

-continued

In another aspect of the invention, there are provided pharmaceutical compositions comprising a therapeutically effective amount of at least one compound of the invention described herein in a pharmaceutically acceptable carrier.

In another aspect of the invention, there are provided compounds that selectively agonize FPR1 compared to FPR2, and uses thereof. In further aspects, the compound shows at least 2-fold selectivity for FPR1 compared to FPR2, or at least 5-fold selectivity for FPR1 compared to FPR2. In yet further aspects, the compound shows at least 10-fold selectivity, at least 20-fold selectivity, at least 50-fold selectivity for FPR1 compared to FPR2, at least 100-fold selectivity for FPR1 compared to FPR, or at least 200-fold selectivity for FPR1 compared to FPR2. In the preceding aspects, the selectivity is reported based on the ratio of the $EC_{50}$ for agonizing FPR2 to the $E_{O50}$ for agonizing FPR1.

In yet another aspect of the invention, there are provided methods for treating disorders associated with FPR modulation, such as FPR1 and FPR2 agonism, or FPR1 agonism, or selective agonism of FPR1 relative to FPR2. In other aspects, there are provided uses of compounds of the invention for treating disorders associated with FPR modulation, such as FPR1 and FPR2 agonism, or FPR1 agonism, or selective agonism of FPR1 relative to FPR2. Such methods and uses can be performed, for example, by administering to a subject in need thereof a therapeutically effective amount of at least one compound of the invention, or by administering a pharmaceutical composition containing a therapeutically effective amount of at least one compound of the invention. In some aspects, the disorder is an inflammatory disease or condition. In further aspects, the inflammatory disease or condition is an ocular inflammatory disease or condition, such as dry eye or post-surgical inflammation, including post-cataract surgical inflammation. In yet further aspects, the inflammatory disease or condition is a dermal inflammatory disease or condition, such as psoriasis or rosacea. In other aspects, the inflammatory disease or condition is a dermal wound, which is treated by administering at least one compound of the invention, or a pharmaceutical composition containing at least one compound of the invention. In other aspects, the disease or condition is a gastrointestinal disease or condition, such as inflammatory bowel disease. In further aspects still, the subject being treated is a mammal, such as a human or non-human primate.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

The term "alkyl", as used herein, refers to saturated, monovalent hydrocarbon moieties having linear or branched moieties or combinations thereof. Alkyl groups typically contain 1 to 6 carbon atoms (i.e., $C_{1-6}$ alkyl), but may contain a variable number of carbon atoms as specified. For example, an alkyl group may comprise 1 to 4 carbon atoms (i.e., $C_{1-4}$ alkyl), or 1 to 3 carbon atoms (i.e., $C_{1-3}$ alkyl). Alkyl groups are optionally substituted with one or more groups including, but not limited to: halogen, hydroxyl, cycloalkyl, heterocycle, aryl, ether, amine, nitro, nitrile, amide, sulfonamide, ester, aldehyde, carboxylic acid, ketone, sulfonic acid, phosphonic acid, and/or phosphoric acid. For example, substituted alkyl includes haloalkyl, such as perhaloalkyl or perfluoroalkyl (e.g., —$CF_3$). In a further example, substituted alkyl includes $C_1$ alkyl substituted with $C_{1-6}$ aryl (e.g., benzyl, which is —$CH_2$-phenyl). One or more methylene ($CH_2$) groups of an alkyl can be replaced by oxygen, sulfur, NH, carbonyl, sulfoxide, sulfonyl, or by a divalent $C_{3-8}$ cycloalkyl; one or more methine (CH) groups of an alkyl can be replaced by nitrogen. Unsubstituted $C_{1-4}$ alkyl includes methyl, ethyl, n-propyl, isopropyl, n-butyl, isobutyl, sec-butyl and t-butyl. Unsubstituted $C_{1-3}$ alkyl includes methyl, ethyl, n-propyl and isopropyl.

The term "alkylene" as used herein refers to a bivalent saturated aliphatic radical derived from an alkene by opening of the double bond, or from an alkane by removal of two hydrogen atoms from different carbon atoms. An alkylene may comprise 1 to 8 carbon atoms (i.e., $C_{1-8}$ alkylene), for example, a $C_1$ alkylene is methylene (—$CH_2$—); a $C_2$ alkylene is ethylene (—$CH_2CH_2$—), and so on.

The term "cycloalkyl", as used herein, refers to a monovalent or divalent group of 3 to 8 carbon atoms (i.e., $C_{3-8}$ cycloalkyl) derived from a saturated cyclic hydrocarbon. Cycloalkyl groups can be monocyclic or polycyclic. Cycloalkyl groups are optionally substituted with one or more groups including, but not limited to: halogen, hydroxyl, alkyl, cycloalkyl, heterocycle, aryl, ether, amine, nitro, nitrile, amide, sulfonamide, ester, aldehyde, carboxylic acid, ketone, sulfonic acid, phosphonic acid, and/or phosphoric acid.

The term "cycloalkenyl", as used herein, refers to a monovalent or divalent group of 3 to 8 carbon atoms (i.e., $C_{3-8}$ cycloalkenyl) derived from a saturated cycloalkyl having one or more double bonds. Cycloalkenyl groups can be monocyclic or polycyclic. Cycloalkenyl groups are optionally substituted by one or more groups including, but not limited to: halogen, hydroxyl, alkyl, cycloalkyl, heterocycle, aryl, ether, amine, nitro, nitrile, amide, sulfonamide, ester, aldehyde, carboxylic acid, ketone, sulfonic acid, phosphonic acid, and/or phosphoric acid.

The term "heterocycle" as used herein, refers to a 3 to 10 membered ring, which can be aromatic (i.e., a heteroaryl) or non-aromatic, saturated or unsaturated, containing at least one heteroatom selected from O, N and S, or combinations of at least two thereof, interrupting the carbocyclic ring structure. The heterocyclic ring can be interrupted by one or more C=O; the S and/or N heteroatom can be oxidized.

Heterocycles can be monocyclic or polycyclic. Heterocyclic ring moieties are optionally substituted with one or more groups including, but not limited to: halogen, hydroxyl, alkyl, —$(CH_2)_{1-6}OH$, —$(CH_2)_{1-6}NH_2$, —$(CH_2)_{1-6}NH(C_{1-6}$ alkyl), —$(CH_2)_{1-6}N(C_{1-6}$ alkyl)$_2$ (wherein each $C_{1-6}$ alkyl is the same or different), haloalkyl, cycloalkyl, heterocycle, aryl, ether, amino, alkylamino, nitro, nitrile, amide, sulfonamide, ester, aldehyde, carboxylic acid, ketone, sulfonic acid, phosphonic acid, and/or phosphoric acid.

The term "aryl" as used herein, refers to an aromatic hydrocarbon ring containing 6 to 10 carbon atoms (i.e., $C_{6-10}$ aryl). Aryl groups are optionally substituted by one or more groups including, but not limited to: halogen, hydroxyl, alkyl, cycloalkyl, heterocycle, aryl, ether, amine, nitro, nitrile, amide, sulfonamide, ester, aldehyde, carboxylic acid, ketone, sulfonic acid, phosphonic acid, and/or phosphoric acid. Aryl can be monocyclic or polycyclic.

The term "halogen", as used herein, refers to an atom of chlorine, bromine, fluorine and/or iodine.

The term "amine" or "amino" as used herein, represents a group of formula "—$NR^xR^y$", wherein $R^x$ and $R^y$ can be the same or independently H, alkyl, aryl, cycloalkyl, cycloalkenyl or heterocyclyl, as defined above.

The term "amide" as used herein, represents a group of formula "—$C(O)N(R^x)(R^y)$" or "—$NR^xC(O)R^y$" wherein $R^x$ and $R^y$ can be the same or independently H, alkyl, aryl, cycloalkyl, cycloalkenyl or heterocyclyl, as defined above.

The term "sulfonamide" as used herein, represents a group of formula "—$S(O)_2N(R^x)(R^y)$" or "—$NR^xS(O)_2R^y$" wherein $R^x$ and $R^y$ can be the same or independently H, alkyl, aryl, cycloalkyl, cycloalkenyl or heterocyclyl, as defined above.

The term "aldehyde" as used herein, represents a group of formula "—$C(O)H$".

The term "ester" as used herein, represents a group of formula "—$C(O)O(R^x)$", wherein $R^x$ is alkyl, aryl, cycloalkyl, cycloalkenyl or heterocyclyl, as defined above.

The term "ketone" as used herein, represents a group of formula "—$C(O)R^x$" wherein $R^x$ is alkyl, aryl, cycloalkyl, cycloalkenyl or heterocyclyl, as defined above.

The term "hydroxyl" as used herein, represents a group of formula "—OH".

The term "carbonyl" as used herein, represents a group of formula "—C(O)—".

The term "carboxyl" as used herein, represents a group of formula "—C(O)O—".

The term "carboxylic acid" as used herein, represents a group of formula "—C(O)OH".

The term "carboxylate" as used herein, represents a group of formula "—C(O)O—".

The term "sulfoxide" as used herein, represents a group of formula "—S(O)—".

The term "sulfonyl" as used herein, represents a group of formula "—$SO_2$—".

The term "sulfate" as used herein, represents a group of formula "—$OS(O)_2O^-$".

The term "sulphonic acid" as used herein, represents a group of formula "—$S(O)_2OH$".

The term "phosphonic acid" as used herein, represents a group of formula "—$P(O)(OH)_2$".

The term "phosphoric acid" as used herein, represents a group of formula "—$(O)P(O)(OH)_2$".

The term "nitro" as used herein, represents a group of formula "—$NO_2$".

The term "nitrile" as used herein, represents a group of formula "—CN".

The term "ether" as used herein, represents a group of formula "—$OR^x$", wherein $R^x$ is alkyl, aryl, cycloalkyl, cycloalkenyl or heterocyclyl, as defined above.

The term "thioether" as used herein, represents a group of formula "—$SR^x$", wherein $R^x$ is alkyl, aryl, cycloalkyl, cycloalkenyl or heterocyclyl, as defined above.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "carboxylate isostere", as used herein, refers to a group that replaces a carboxylic acid, such as a group selected from sulfonate, sulfonic acid, phosphonate, phosphonic acid, phosphoric acid, and unsubstituted or substituted heterocycle, wherein said heterocycle is a 5-membered aromatic heterocycle, preferably selected from tetrazole, imidazole, thiazole, oxazole, triazole, thiophene, pyrazole and pyrole; and wherein said heterocycle substituent is selected from halogen, —$C_{1-6}$ alkyl, —$C_{1-6}$ haloalkyl, —$(CH_2)_{1-6}OH$, —$(CH_2)_{1-6}NH_2$, —$(CH_2)_{1-6}NH(C_{1-6}$ alkyl) and —$(CH_2)_{1-6}N(C_{1-6}$ alkyl$)_2$ (wherein each $C_{1-6}$ alkyl is the same or different).

The term "therapeutically effective amount" means the amount of a pharmaceutical composition that will elicit a biological or medical response in a subject in need thereof that is being sought by the researcher, veterinarian, medical doctor or other clinician.

The term "pharmaceutically acceptable salts" refers to salts or complexes that retain the desired biological activity of compounds of the invention, and exhibit minimal or no undesired toxicological effects. The "pharmaceutically acceptable salts" according to the invention include therapeutically active, non-toxic base or acid salt forms, which the compounds of Formula I, I-A, I-B, I-C and I-D are able to form.

Some compounds of the invention may form salts with acids or bases, including pharmaceutically acceptable acids or bases. Such pharmaceutically acceptable salts of the compounds described herein are within the scope of the invention.

The acid addition salt form of a compound of Formula I, I-A, I-B, I-C and I-D that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic acid and the like. The base addition salt form of a compound of Formula I, I-A, I-B, I-C or I-D that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-arginine, ethanolamine, betaine, benzathine, morpholine and the like. (See Handbook of Pharmaceutical Salts, P. Heinrich Stahl & Camille G. Wermuth (Eds), Verlag Helvetica Chimica Acta, Zürich, 2002, 329-345.)

The compounds of Formula I and some of their intermediates have at least one asymmetric center in their structure. This assymetric center (or chiral center) may be present in an R or S configuration, said R and S notation is used in correspondence with the rules described in *Pure Appl. Chem.* (1976), 45, pp. 11-13. As such, the compounds of Formula I may exist in enantiomeric as well as diastereoisomeric forms. It is intended that all stereoisomeric forms of the compounds of Formula I, as well as mixtures thereof, including racemic mixtures, form part of the present invention. Graphical representation of stereochemical configuration is made in accordance with IUPAC Recommendations (*Pure Appl. Chem.* (2006), 78(10), pp. 1897-1970). Wedge notation is used herein to indicate the absolute stereochemical configuration of a stereocenter. A solid wedge (——) indicates the bond projects above the plane of the paper (towards the viewer), and a hashed wedge (......) indicates the bond projects below the plane of the paper; in both cases, the bonds are oriented with the sharp end pointed at the stereogenic center. A wavy or "squiggly" line (∿∿) indicates that the absolute configuration is unknown.

In addition, the present invention embraces all geometric and positional isomers. For example, if a compound of Formula I incorporates a double bond or a fused ring, both the cis- and trans-forms, as well as mixtures thereof, are embraced within the scope of the invention.

Diastereoisomeric mixtures can be separated into their individual diastereoisomers on the basis of their physicochemical property differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of chiral HPLC, or by chiral supercritical fluid chromatography. Also, some of the compounds of the invention may be atropisomers (e.g., substituted biaryls) and are considered as part of this invention.

In particular, a skilled person will realize that even if the absolute stereochemistry of a particular stereoisomer (e.g., an enantiomer or diastereomer) of a molecule is not known, that particular stereoisomer can be distinguished from the other stereoisomers by use of other techniques (e.g., polarimetry, nuclear magnetic resonance spectroscopy, chromatography, and others identifiable to a skilled person). In particular, one exemplary method of distinguishing stereoisomers when the absolute stereochemistry of each stereoisomer is not known is chromatography, such as flash chromatography, medium pressure chromatography, high pressure liquid chromatography (HPLC), and/or supercritical fluid chromatography. In particular, two or more stereoisomers such as diastereomers can be separated and characterized by their retention times, which would be expected to be replicable by using the same chromatographic conditions (e.g., flow rate, column material, solvent systems/gradient profiles, and/or others identifiable to a skilled person). A skilled person will realize that even when the exact absolute or relative retention times of one or more stereoisomers is not replicated (e.g., due to slight variations in the chromatographic parameters and/or chromatographic equipment), a stereoisomer with a shorter retention time can be recognized and said to be "faster eluting,", "earlier eluting" or having a "high Rf," and a stereoisomer with a longer retention time can be recognized and said to be "slower eluting," "later eluting or having a "low Rf." A skilled person will realize that once two or more stereoisomers are distinguished by a technique such as chromatography, the absolute stereochemistry of the stereoisomers can be determined by techniques or combinations of techniques identifiable to a skilled person (e.g., X-ray crystallography, vibrational circular dichroism, nuclear magnetic resonance, total synthesis, and others identifiable to a skilled person).

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Also, for example, all keto-enol and imine-enamine forms of the compounds are included in the invention. Individual stereoisomers of the compounds of the invention may, for example, be substantially free of other isomers, or may be admixed, for example, as racemates or with all other, or other selected, stereoisomers. The use of the terms "salt", "solvate", and the like, is intended to equally apply to the salt and solvate of enantiomers, stereoisomers, rotamers, tautomers, positional isomers, or racemates of the inventive compounds.

The present invention includes all pharmaceutically acceptable isotopically enriched compounds. Any compound of the invention may contain one or more isotopic atoms enriched or different than the natural ratio, such as deuterium $^2H$ (or D) in place of hydrogen $^1H$ (or H), or use of $^{13}C$ enriched material in place of $^{12}C$ and the like. Similar substitutions can be employed for N, O, S and P. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

In an embodiment of the invention, there are provided pharmaceutical compositions including a therapeutically effective amount of at least one compound of the invention in a pharmaceutically acceptable carrier.

The compounds of the invention and the pharmaceutical compositions comprising at least one compound of the invention are indicated for use in treating or preventing conditions in which there is likely to be a component involving the FPR, such as FPR1 and/or FPR2.

In a further embodiment of the invention, there are provided methods for treating disorders associated with FPR modulation (such as FPR1 and FPR2 agonism, or FPR1 agonism, or selective agonism of FPR1 relative to FPR2). Such methods can be performed, for example, by administering to a subject in need thereof a therapeutically effective amount of at least one compound of the invention, or by administering a pharmaceutical composition comprising a therapeutically effective amount of at least one compound of the invention.

More specifically, the present invention provides for:

use of a compound of the invention for the treatment of a mammalian subject (including a human subject) having one or more diseases or conditions that are alleviated by FPR modulation (such as FPR1 and FPR2 agonism, or FPR1 agonism, or selective agonism of FPR1 relative to FPR2); and/or a method of treating a mammalian subject (including a human subject) having one or more diseases or conditions that are alleviated by FPR modulation (such as FPR1 and FPR2 agonism, or FPR1 agonism, or selective agonism of FPR1 relative to FPR2);

wherein the disease or condition is an ocular inflammatory disease, including but not limited to: age-related macular degeneration, wet macular degeneration, dry macular degeneration, uveitis, dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity, acute macular neuroretinopathy, central serous chorioretinopathy, cystoid macular edema, and diabetic macular edema; infectious keratitis, herpetic keratitis, corneal angiogenesis, lymphangiogenesis, uveitis, retinitis, choroiditis, such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, bone marrow transplant retinopathy, corneal wound healing, post-surgical corneal wound healing and/or inflammation, and post-cataract surgical inflammation; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, blepharitis, meibomian gland dysfunction (MDG), glaucoma, branch vein occlusion, Best's vitelliform macular degeneration, retinitis pigmentosa, proliferative vitreoretinopathy (PVR), and any other degenerative disease of either the photoreceptors or the retinal pigment epithelium (Perretti, Mauro et al. Pharmacology & Therapeutics 127 (2010) 175-188).

In other embodiments, the present invention provides for:

use of a compound of the invention for the treatment of a mammalian subject (including a human subject) having one or more diseases or conditions that are alleviated by FPR modulation (such as FPR1 and FPR2 agonism, or FPR1 agonism, or selective agonism of FPR1 relative to FPR2); and/or a method of treating a mammalian subject (including a human subject) having one or more diseases or conditions that are alleviated by FPR modulation (such as FPR1 and FPR2 agonism, or FPR1 agonism, or selective agonism of FPR1 relative to FPR2);

wherein the disease or condition is a dermal inflammatory disease or condition, including, but not limited to: dermal wound healing, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, disorders of pigmentation, alopecia, scarring and non-scarring forms.

In yet other embodiments, the present invention provides for:

use of a compound of the invention for the treatment of a mammalian subject (including a human subject) having one or more diseases or conditions that are alleviated by FPR modulation (such as FPR1 and FPR2 agonism, or FPR1 agonism, or selective agonism of FPR1 relative to FPR2); and/or a method of treating a mammalian subject (including a human subject) having one or more diseases or conditions that are alleviated by FPR modulation (such as FPR1 and FPR2 agonism, or FPR1 agonism, or selective agonism of FPR1 relative to FPR2);

wherein the disease or condition is stroke, coronary artery disease, a cardiovascular disorder, coronary artery disease or angina pectoris; or an obstructive airway disease; or a neurological disorder, Alzheimer's disease, neuroinflammation or pain; or an HIV-mediated retroviral infection; or an immunological disorder, arthritis, rheumatoid arthritis, systemic lupus erythematosus or multiple sclerosis; or sepsis; or inflammatory bowel disease (IBD) and/or IBD pain, Crohn's disease, or ulcerative colitis; or asthma or an allergic disorder; or cachexia.

In a further embodiment of the invention, the method of treating a disease or condition alleviated by FPR modulation (such as FPR1 and FPR2 agonism, or FPR1 agonism, or selective agonism of FPR1 relative to FPR2), comprises administering to the subject in need of the treatment a therapeutically effective amount of at least one compound of the invention, or an enantiomer, diastereomer or tautomer thereof, or any mixture thereof in any ratio; or pharmaceutically acceptable salt of any one of the foregoing; thereby treating the disease or condition.

In a further embodiment of the invention, the method of treating a disease or condition alleviated by FPR modulation (such as FPR1 and FPR2 agonism, or FPR1 agonism, or selective agonism of FPR1 relative to FPR2), comprises administering to the subject in need of the treatment a pharmaceutical composition comprising a therapeutically effective amount of at least one compound of the invention, or an enantiomer, diastereomer or tautomer thereof, or any mixture thereof in any ratio; or pharmaceutically acceptable salt of any one of the foregoing; thereby treating the disease or condition.

In one embodiment, the invention provides for a method of treating a disease or condition in a subject in need of such treatment, the method comprising administering a therapeutically effective amount of a compound of Formula I, I-A, I-B, I-C and/or I-D, to the subject (or a pharmaceutical composition comprising a therapeutically effective amount of a compound of Formula I, I-A, I-B, I-C and/or I-D to the subject), thereby treating the disease or condition. In one embodiment, the method comprises administering a compound of Formula I. In another embodiment, the method comprises administering a compound of Formula I-A. In another embodiment, the method comprises administering a compound of Formula I-B. In another embodiment, the method comprises administering a compound of Formula I-C. In another embodiment, the method comprises administering a compound of Formula I-D. In another embodiment, the method comprises administering a therapeutically effective compound of Formula 1-A, Formula 1-B, Formula 1-C, Formula I-D, or a mixture of any combination of two or more of the foregoing in any ratio.

In a further embodiment, the disease or condition is an ocular inflammatory disease or condition. In a further embodiment, the disease or condition is an ocular inflammatory disease or condition selected from: age-related macular degeneration, wet macular degeneration, dry macular degeneration, uveitis, dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity, acute macular neuroretinopathy, central serous chorioretinopathy, cystoid macular edema, and diabetic macular edema; infectious keratitis, herpetic keratitis, corneal angiogenesis, lymphangiogenesis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, bone marrow transplant retinopathy, post-surgical corneal wound healing or inflammation, and post-cataract surgical inflammation; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, corneal wound healing burns, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degeneration, retinitis pigmentosa, proliferative vitreoretinopathy (PVR), and any other degenerative disease of either the photoreceptors or the retinal pigment epithelium. In a further embodiment, the ocular inflammatory disease or condition is selected from: dry eye, a post-surgical corneal wound, post-surgical corneal inflammation, and post-cataract surgical inflammation.

In a further embodiment, there is provided the method of treating the disease or condition associated with FPR modulation, such as FPR1 and FPR2 agonism, or FPR1 agonism, or selective agonism of FPR1 relative to FPR2, wherein the disease or condition is a dermal inflammatory disease or condition. In a further embodiment, the dermal inflammatory disease or condition is selected from: a dermal wound, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, disorders of pigmentation, alopecia, scarring and non-scarring forms. In a further embodiment, the dermal inflammatory disease or condition is psoriasis or rosacea.

In a further embodiment, there is provided the method of treating the disease or condition associated with FPR modulation, such as FPR1 and FPR2 agonism, or FPR1 agonism, or selective agonism of FPR1 relative to FPR2, wherein the disease or condition is selected from wherein the disease or condition is stroke, coronary artery disease, a cardiovascular disorder, coronary artery disease or angina pectoris; or an obstructive airway disease; or a neurological disorder, Alzheimer's disease, neuroinflammation or pain; or an HIV-mediated retroviral infection; or an immunological disorder, arthritis, rheumatoid arthritis, systemic lupus erythematosus, multiple sclerosis; or sepsis; or inflammatory bowel disease or ulcerative colitis; or asthma or an allergic disorder; or cachexia. In one embodiment, the disease or condition is rheumatoid arthritis. In one embodiment, the disease or condition is multiple sclerosis. In another embodiment, the disease or condition is inflammatory bowel disease. In one embodiment, the disease or condition is ulcerative colitis.

In one embodiment, there is provided the method of any one of the preceding embodiments, wherein the subject is a human.

The actual amount of the compound to be administered in any given case will be determined by a physician taking into account the relevant circumstances, such as the severity of the condition, the age and weight of the subject/patient, the patient's general physical condition, the cause of the condition, and the route of administration.

The subject will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back of the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains a therapeutically effective amount of one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition, auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose, any bland fixed oil may be employed, including synthetic monoor diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions.

Pharmaceutical compositions may be in a form suitable for topical dermatological application of a therapeutically effective dose; non-limiting examples of such suitable forms include suspensions, gels, solutions, creams, lotions, ointments, foams, emulsions, microemulsions, milks, serums, aerosols, sprays, dispersions, microcapsules, vesicles, microparticles, and cloths, such as wet cloths, dry cloths or facial cloths. The pharmaceutical composition may comprise excipients, binders, lubricants, solvents, disintegrants, or enhancers of cutenous penetration. The pharmaceutically acceptable excipients may include one or more skin-penetrating agents, moisturizers, preservatives, gelling agents, protective agents, oil-in-water, water-in-oil, water-in-oil-in-water, and oil-in-water-in-silicon emulsions. The active ingredient is used in an amount of about 0.01% up to about 20% and preferably about 0.1% to about 10% by weight based on the total weight of the composition. Emulsions, such as creams and lotions that can be used as topical carriers and their preparation are disclosed in Remington: The Science and Practice of Pharmacy 282-291 (Alfonso R. Gennaro Ed. 19$^{th}$ ed. 1995) hereby incorporated herein by reference. Suitable gels for use in the invention are disclosed in Remington: The Science and Practice of Pharmacy 1517-1518 (Alfonso R. Gennaro Ed. 19$^{th}$ ed. 1995) hereby incorporated herein by reference. Other suitable gels for use within the invention are disclosed in U.S. Pat. Nos. 6,387,383, 6,517,847 and 6,468,989.

Pharmaceutical compositions may be prepared by combining a therapeutically effective amount of at least one compound according to the present invention, or a pharmaceutically acceptable salt thereof, as an active ingredient with conventional pharmaceutical excipients and by preparation of unit dosage suitable for topical use (for example, dermatological or ocular use). The therapeutically efficient amount typically is between about 0.001 and about 5% (w/v), preferably about 0.001 to about 2.0% (w/v) in liquid formulations.

For ophthalmic application, the pharmaceutical excipient is an ophthalmically acceptable excipient. Preferably, solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.8 |
| antioxidant | as needed |
| surfactant | as needed |
| purified water | to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses. Preservative-free solutions are often formulated in non-resalable containers containing up to about ten, preferably up to about five units doses, where a typical unit dose is from one to about 8 drops, preferably one to about 3 drops. The volume of one drop usually is about 20-35 microliters.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

In one embodiment, the invention provides for a pharmaceutical composition comprising as active ingredient a therapeutically effective amount of a compound of Formula I, I-A, I-B, I-C, I-D, or a mixture of any combination of any two or more of the foregoing in any ratio, and a pharmaceutically acceptable carrier. In a further embodiment, there is provided the pharmaceutical composition for use in treating an inflammatory disease or condition in a subject in need of such treatment, wherein the disease or condition is an ocular inflammatory disease or condition, or a dermal inflammatory disease or condition.

Each and every feature described herein, and each and every combination of two or more of such features, is included within the scope of the present invention provided that the features included in such a combination are not mutually inconsistent.

The following are non-limiting embodiments of the invention.

In embodiment (1), there is provided a compound of Formula I:

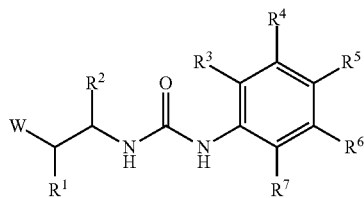

Formula I wherein:
W is —COOH, —C(O)OR$^a$, sulfonate, sulfonic acid, phosphonate, phosphonic acid, phosphoric acid, boronic acid or Het$^1$;
wherein R$^a$ is optionally substituted C$_{1-6}$ alkyl, wherein said optional substituent is selected from the group consisting of —OH, halogen, —OC$_{1-8}$ alkyl and (OC$_{1-8}$ alkylene)$_q$-OC$_{1-8}$alkyl, wherein q is 1, 2, 3, 4, 5 or 6; and wherein Het$^1$ is a 5-membered aromatic heterocycle optionally substituted with one or more halogen, unsubstituted —C$_{1-6}$ alkyl, —C$_{1-6}$ haloalkyl, —OC$_{1-6}$ alkyl, —(CH$_2$)$_{1-6}$OH, —(CH$_2$)$_{1-6}$NH$_2$, —(CH$_2$)$_{1-6}$NH(C$_{1-6}$alkyl) or —(CH$_2$)$_{1-6}$NR$^{14}$R$^{15}$,
R$^1$ is optionally substituted C$_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{14}$R$^{15}$, urea, —COOH, —C(O)OC$_{1-6}$ alkyl, —C(O)NH$_2$, optionally substituted C$_{3-8}$ cycloalkyl, optionally substituted C$_{3-8}$ cycloalkenyl, optionally substituted C$_{6-10}$ aryl, and optionally substituted heterocycle;
R$^2$ is optionally substituted C$_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{14}$R$^{15}$, urea, —COOH, —C(O)OC$_{1-6}$ alkyl, —C(O)NH$_2$, optionally substituted C$_{3-8}$ cycloalkyl, optionally substituted C$_{3-8}$ cycloalkenyl, optionally substituted C$_{6-10}$ aryl, and optionally substituted heterocycle;
R$^3$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^8$, —S(O)$_m$R$^{10}$, —C(O)R$^{11}$, —SR$^{12}$ or —OR$^{12}$,
R$^4$ is H, optionally substituted C$_{1-6}$ alkyl, C$_{1-6}$ haloalkyl, halogen, —S(O)$_m$R$^{10}$ or —C(O)R$^{11}$,
R$^5$ is optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —S(O)$_m$R$^{10}$, —C(O)R$^{11}$, —SR$^{13}$ or —OR$^{13}$,
R$^6$ is H, optionally substituted C$_{1-6}$ alkyl, C$_{1-6}$ haloalkyl, halogen, —S(O)$_m$R$^{10}$ or —C(O)R$^{11}$,
R$^7$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^8$, —S(O)$_m$R$^{10}$, —C(O)R$^{11}$, —SR$^{12}$ or —OR$^{12}$;
R$^8$ is H, optionally substituted C$_{1-6}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^9$ is H, optionally substituted C$_{1-6}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^{19}$ is —OH, optionally substituted C$_{1-6}$ alkyl or optionally substituted C$_{6-10}$ aryl;
R$^{11}$ is —OH, optionally substituted C$_{1-6}$ alkyl or optionally substituted C$_{6-10}$ aryl;
R$^{12}$ is H or optionally substituted C$_{1-8}$ alkyl;
R$^{13}$ is H, optionally substituted C$_{1-8}$ alkyl, optionally substituted C$_{3-8}$cycloalkyl, optionally substituted C$_{3-8}$ cycloalkenyl, optionally substituted C$_{6-10}$ aryl or optionally substituted heterocycle;
R$^{14}$ is C$_{1-6}$alkyl,
R$^{15}$ is C$_{1-6}$ alkyl; and
each m is independently 1 or 2;
or a mixture of two or more diastereomers thereof;
or a mixture of enantiomers thereof;
or an individual enantiomer or diastereoisomer thereof;
or a pharmaceutically acceptable salt of any of the foregoing;
provided that the compound is not:

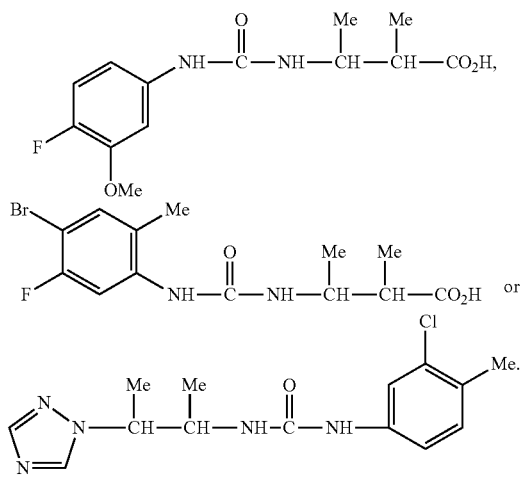

In embodiment (2), there is provided the compound of embodiment (1), wherein W is COOH, sulfonate, sulfonic acid, phosphonate, phosphonic acid, phosphoric acid or Het$^1$, wherein Het$^1$ is tetrazole, imidazole, thiazole, oxazole, triazole, isoxazole, oxadiazole, thiadiazole, thiophene, pyrazole or pyrrole; preferably, W is COOH.

In embodiment (3), there is provided the compound of embodiment (1) or (2), wherein R$^1$ is unsubstituted C$_{2-6}$ alkyl.

In embodiment (4), there is provided the compound of embodiment (3), wherein R$^2$ is unsubstituted C$_{1-3}$ alkyl, preferably methyl.

In embodiment (5), there is provided the compound of embodiment (4), wherein R$^2$ is methyl, and R$^5$ is C$_{1-6}$ haloalkyl or halogen.

In embodiment (6), there is provided the compound of any one of embodiments (1) through (5), wherein W is COOH.

In embodiment (7), there is provided the compound of embodiment (1), wherein each of R$^4$ and R$^6$ is H.

In embodiment (8), there is provided the compound of embodiment (2), wherein:

$R^1$ is unsubstituted $C_{2-6}$ alkyl;
$R^2$ is methyl;
$R^3$ is H or F;
$R^4$ is H;
$R^5$ is $C_{1-6}$ haloalkyl or halogen;
$R^6$ is H; and
$R^7$ is H or F.

In embodiment (9), there is provided the compound of embodiment (1), (2) or (8), wherein $R^1$ is unsubstituted ethyl, n-propyl, isopropyl, n-butyl, sec-butyl, isobutyl or tert-butyl.

In embodiment (10), there is provided the compound of embodiment (1), (2) or (8), wherein $R^1$ is isopropyl, n-butyl, sec-butyl, isobutyl or tert-butyl.

In embodiment (11), there is provided the compound of embodiment (1), (2) or (8), wherein $R^1$ is isopropyl or isobutyl, and $R^2$ is methyl.

In embodiment (12), there is provided the compound of embodiment (1), (2) or (8), wherein $R^1$ has the following structure:

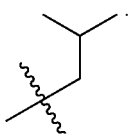 [SMILES: *CC(C)C]

In embodiment (13), there is provided the compound of embodiment (1) or (2), wherein $R^1$ is unsubstituted benzyl; provided that $R^1$ and $R^2$ are not the same.

In embodiment (14), there is provided the compound of embodiment (1), wherein W is —COOH or —C(O)OR$^a$.

In embodiment (15), there is provided the compound of embodiment (1) or (14), wherein W is —C(O)OR$^a$, preferably, $R^a$ is unsubstituted $C_{1-6}$ alkyl; optionally, the compound is a prodrug, wherein the ester is hydrolyzed in vivo to provide the corresponding carboxylic acid.

In embodiment (16), there is provided the compound of embodiment (1), (2) or (8), wherein W is unsubstituted Het$^1$, preferably triazole.

In embodiment (17), there is provided the compound of embodiment (1), (2) or (8), wherein $R^5$ is $C_{1-6}$ haloalkyl, F, Cl or Br; preferably, $R^5$ is —CF$_3$ or Br; most preferably, $R^5$ is Br.

In embodiment (18), there is provided the compound of embodiment (1) or (2), wherein:
$R^1$ is unsubstituted ethyl, n-propyl, isopropyl, n-butyl, sec-butyl, isobutyl or tert-butyl;
$R^2$ is methyl;
$R^3$ is H;
$R^4$ is H;
$R^5$ is —CF$_3$, fluorine, chlorine or bromine;
$R^6$ is H; and
$R^7$ is H.

In embodiment (19), there is provided the compound of embodiment (18), wherein:
$R^1$ is unsubstituted n-propyl, isopropyl, n-butyl, sec-butyl, isobutyl or tert-butyl, preferably $R^1$ is isobutyl; and
$R^5$ is —CF$_3$ or bromine.

In embodiment (20), there is provided the compound of embodiment (1), (2), (14) or (15), wherein:
$R^1$ is unsubstituted $C_{2-6}$ alkyl, preferably isopropyl or isobutyl;
$R^2$ is methyl;
$R^3$ is H or F;
$R^4$ is H;
$R^5$ is $C_{1-6}$ haloalkyl or halogen, preferably —CF$_3$ or bromine;
$R^6$ is H; and
$R^7$ is H or F.

In embodiment (21), there is provided a compound which is:

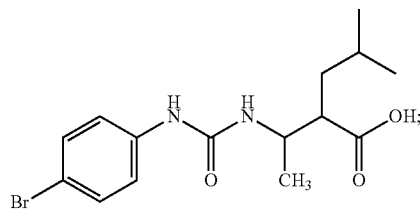 [SMILES: CC(C)CC(C(=O)O)C(C)NC(=O)Nc1ccc(Br)cc1]

or a mixture of two or more diastereomers thereof;
or a mixture of enantiomers thereof;
or an individual enantiomer or diastereoisomer thereof;
or a pharmaceutically acceptable salt of any of the foregoing;

In embodiment (22), there is provided a compound of embodiment (21) selected from the group consisting of:

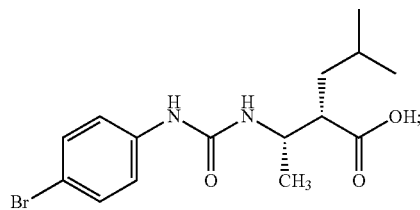 [SMILES: CC(C)C[C@H](C(=O)O)[C@H](C)NC(=O)Nc1ccc(Br)cc1]

(S)-2-((S)-1-(3-(4-bromophenyl)ureido)ethyl)-4-methylpentanoic acid

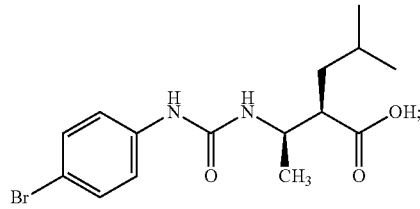 [SMILES: CC(C)C[C@@H](C(=O)O)[C@@H](C)NC(=O)Nc1ccc(Br)cc1]

(R)-2-((R)-1-(3-(4-bromophenyl)ureido)ethyl)-4-methylpentanoic acid

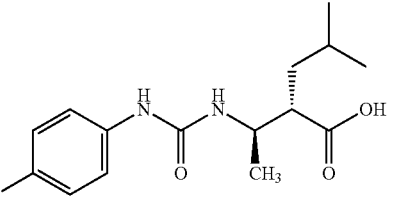

(S)-2-((R)-1-(3-(4-bromophenyl)ureido)ethyl)-4-methylpentanoic acid

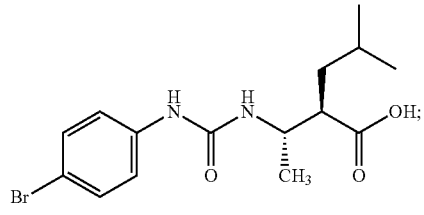

(R)-2-((S)-1-(3-(4-bromophenyl)ureido)ethyl)-4-methylpentanoic acid and a mixture of any two or more of the foregoing;
and pharmaceutically acceptable salts thereof.

In embodiment (23), there is provided the compound of embodiment (22) selected from the group consisting of:

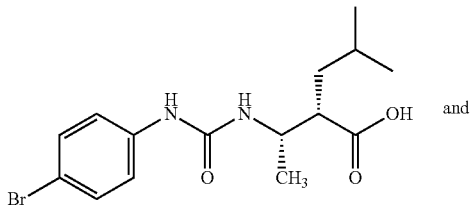

and

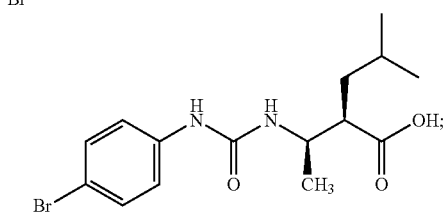

and a mixture thereof;
and pharmaceutically acceptable salts thereof.

In embodiment (24), there is provided a compound of embodiment (23), wherein the mixture is a racemic mixture; or a pharmaceutically acceptable salt thereof.

In embodiment (25), there is provided a compound of embodiment (22) which is:

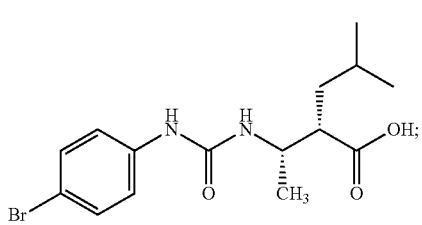

or a pharmaceutically acceptable salt thereof.

In embodiment (26), there is provided a compound of embodiment (22) which is:

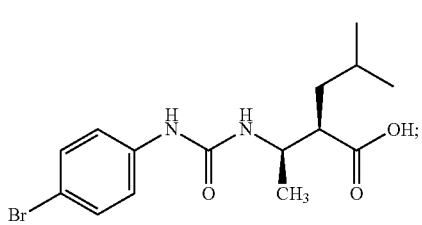

or a pharmaceutically acceptable salt thereof.

In embodiment (27), there is provided a compound of embodiment (22) selected from the group consisting of:

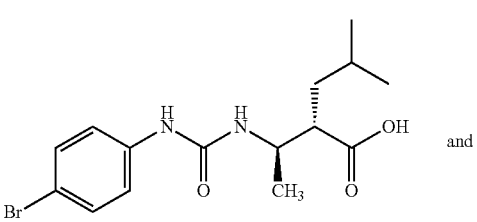

and

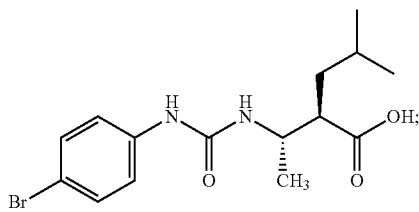

and a mixture thereof;
and pharmaceutically acceptable salts thereof.

In embodiment (28), there is provided the compound of embodiment (27), wherein the mixture is a racemic mixture; or a pharmaceutically acceptable salt thereof.

In embodiment (29), there is provided a compound of embodiment (22) which is:

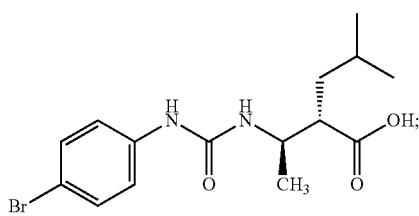 [SMILES: CC(C)C[C@H](C(=O)O)[C@@H](C)NC(=O)Nc1ccc(Br)cc1]

or a pharmaceutically acceptable salt thereof.

In embodiment (30), there is provided a compound of embodiment (22) which is:

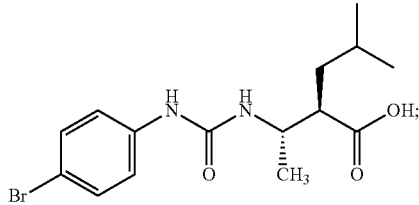 [SMILES: CC(C)C[C@@H](C(=O)O)[C@H](C)NC(=O)Nc1ccc(Br)cc1]

or a pharmaceutically acceptable salt thereof.

In embodiment (31), there is provided the following compound:

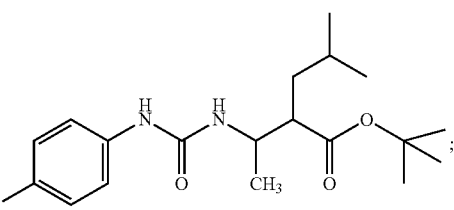

or a mixture of two or more diastereomers thereof;
or a mixture of enantiomers thereof;
or an individual enantiomer or diastereoisomer thereof;
or a pharmaceutically acceptable salt of any of the foregoing;

In embodiment (32), there is provided a compound of embodiment (31) selected from the group consisting of:

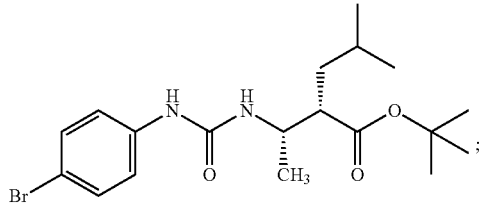 [SMILES: CC(C)CC(C(=O)OC(C)(C)C)C(C)NC(=O)Nc1ccc(Br)cc1]

(S)-tert-butyl 2-((S)-1-(3-(4-bromophenyl)ureido)ethyl)-4-methylpentanoate

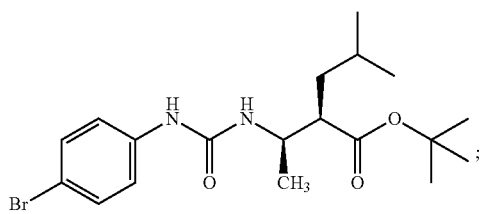

(R)-tert-butyl 2-((R)-1-(3-(4-bromophenyl)ureido)ethyl)-4-methylpentanoate

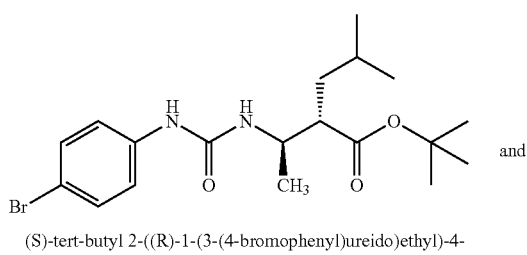
and (S)-tert-butyl 2-((R)-1-(3-(4-bromophenyl)ureido)ethyl)-4-methylpentanoate

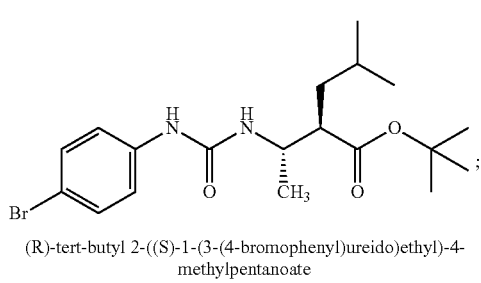

(R)-tert-butyl 2-((S)-1-(3-(4-bromophenyl)ureido)ethyl)-4-methylpentanoate and a mixture of any two or more of the foregoing;
and pharmaceutically acceptable salts thereof.

In embodiment (33), there is provided a compound of embodiment (32) selected from the group consisting of:

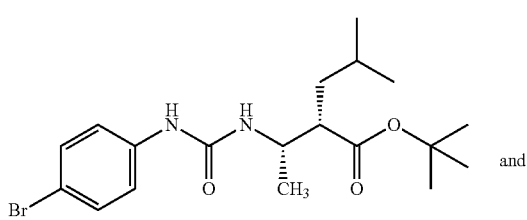
and

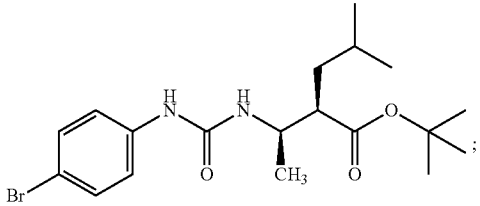
;

and a mixture thereof;
and pharmaceutically acceptable salts thereof.

In embodiment (34), there is provided the compound of embodiment (33), wherein the mixture is a racemic mixture; or a pharmaceutically acceptable salt thereof.

In embodiment (35), there is provided a compound of embodiment (32) which is:

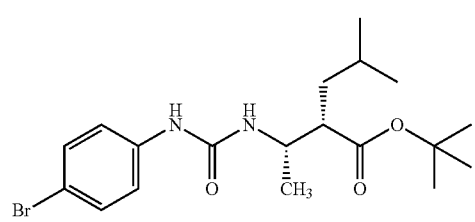 [SMILES: CC(C)C[C@H](C(=O)OC(C)(C)C)[C@H](C)NC(=O)Nc1ccc(Br)cc1]

or a pharmaceutically acceptable salt thereof.

In embodiment (36), there is provided a compound of embodiment (32) which is:

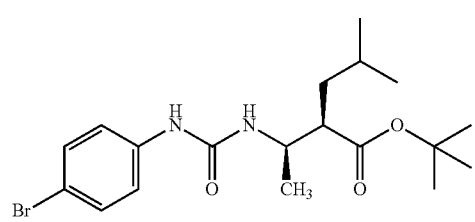 [SMILES: CC(C)C[C@@H](C(=O)OC(C)(C)C)[C@@H](C)NC(=O)Nc1ccc(Br)cc1]

or a pharmaceutically acceptable salt thereof.

In embodiment (37), there is provided a compound of embodiment (32) selected from the group consisting of:

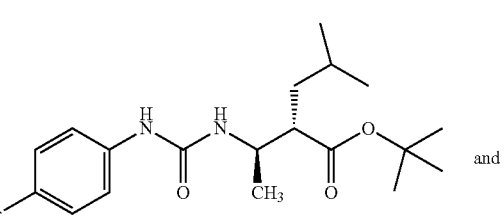
and

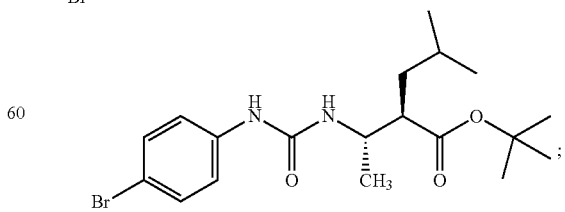
;

and a mixture thereof;
and pharmaceutically acceptable salts thereof.

In embodiment (38), there is provided the compound of embodiment (37), wherein the mixture is a racemic mixture; or a pharmaceutically acceptable salt thereof.

In embodiment (39), there is provided a compound of embodiment (32) which is:

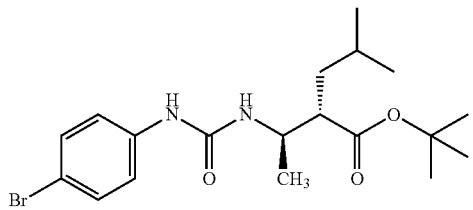 [SMILES: CC(C)C[C@H](C(=O)OC(C)(C)C)[C@@H](C)NC(=O)Nc1ccc(Br)cc1]

or a pharmaceutically acceptable salt thereof.

In embodiment (40), there is provided a compound of embodiment (32) which is:

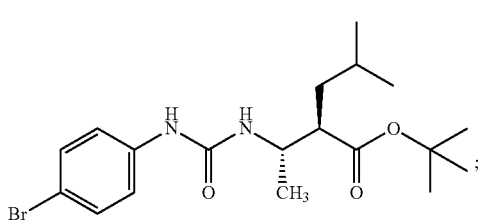 [SMILES: CC(C)C[C@@H](C(=O)OC(C)(C)C)[C@H](C)NC(=O)Nc1ccc(Br)cc1]

or a pharmaceutically acceptable salt thereof.

In embodiment (I a), there is provided a compound of Formula I-A, Formula 1-B, or a mixture thereof:

Formula I-A

Formula I-B

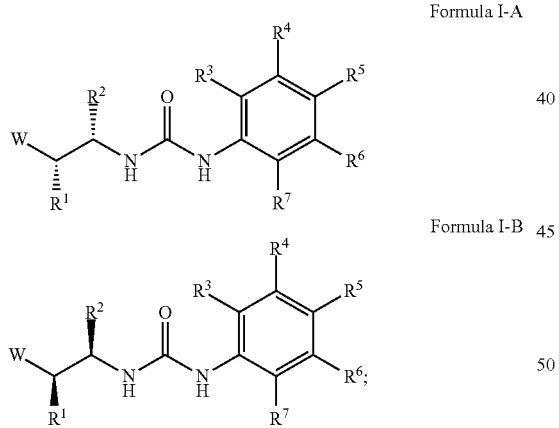

wherein:
W is —COOH, —C(O)OR$^a$, sulfonate, sulfonic acid, phosphonate, phosphonic acid, phosphoric acid, boronic acid or Het$^1$;
wherein R$^a$ is optionally substituted $C_{1-6}$ alkyl, wherein said optional substituent is selected from the group consisting of —OH, halogen, —OC$_{1-8}$ alkyl and —(OC$_{1-8}$ alkylene)$_q$-OC$_{1-8}$ alkyl, wherein q is 1, 2, 3, 4, 5 or 6; and wherein Het$^1$ is a 5-membered aromatic heterocycle optionally substituted with one or more halogen, unsubstituted —C$_{1-6}$ alkyl, —C$_{1-6}$ haloalkyl, —OC$_{1-6}$alkyl, —(CH$_2$)$_{1-6}$OH, —(CH$_2$)$_{1-6}$NH$_2$, —(CH$_2$)$_{1-6}$NH(C$_{1-6}$ alkyl) or —(CH$_2$)$_{1-6}$NR$^{14}$R$^{15}$;

R$^1$ is optionally substituted $C_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{14}$R$^{15}$, urea, —COOH, —C(O)OC$_{1-6}$ alkyl, —C(O)NH$_2$, optionally substituted $C_{3-8}$ cycloalkyl, optionally substituted $C_{3-8}$ cycloalkenyl, optionally substituted $C_{6-10}$ aryl, and optionally substituted heterocycle;

R$^2$ is optionally substituted $C_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{14}$R$^{15}$, urea, —COOH, —C(O)OC$_{1-6}$ alkyl, —C(O)NH$_2$, optionally substituted $C_{3-8}$ cycloalkyl, optionally substituted $C_{3-8}$ cycloalkenyl, optionally substituted $C_{6-10}$ aryl, and optionally substituted heterocycle;

R$^3$ is H, optionally substituted $C_{1-6}$ alkyl, $C_{1-6}$ haloalkyl, optionally substituted $C_{3-8}$ cycloalkyl, optionally substituted $C_{3-8}$ cycloalkenyl, optionally substituted $C_{6-10}$ aryl, optionally substituted heterocycle, halogen, —NR$^8$R$^9$, —S(O)$_m$R$^{10}$, —C(O)R$^{11}$, —SR$^{12}$ or —OR$^{12}$, R$^4$ is H, optionally substituted $C_{1-6}$ alkyl, $C_{1-6}$ haloalkyl, halogen, —S(O)$_m$R$^{10}$ or —C(O)R$^{11}$, R$^5$ is optionally substituted $C_{1-6}$ alkyl, $C_{1-6}$ haloalkyl, optionally substituted $C_{3-8}$ cycloalkyl, optionally substituted $C_{3-8}$ cycloalkenyl, optionally substituted $C_{6-10}$ aryl, optionally substituted heterocycle, halogen, —S(O)$_m$R$^{10}$, —C(O)R$^{11}$, —SR$^{13}$ or —OR$^{13}$, R$^6$ is H, optionally substituted $C_{1-6}$ alkyl, $C_{1-6}$ haloalkyl, halogen, —S(O)$_m$R$^{10}$ or —C(O)R$^{11}$, R$^7$ is H, optionally substituted $C_{1-6}$ alkyl, $C_{1-6}$ haloalkyl, optionally substituted $C_{3-8}$ cycloalkyl, optionally substituted $C_{3-8}$ cycloalkenyl, optionally substituted $C_{6-10}$ aryl, optionally substituted heterocycle, halogen, —NR$^8$R$^9$, —S(O)$_m$R$^{10}$, —C(O)R$^{11}$, —SR$^{12}$ or —OR$^{12}$, R$^8$ is H, optionally substituted $C_{1-6}$ alkyl, optionally substituted $C_{3-8}$ cycloalkyl, optionally substituted $C_{3-8}$ cycloalkenyl, optionally substituted $C_{6-10}$ aryl or optionally substituted heterocycle;

R$^9$ is H, optionally substituted $C_{1-6}$ alkyl, optionally substituted $C_{3-8}$ cycloalkyl, optionally substituted $C_{3-8}$ cycloalkenyl, optionally substituted $C_{6-10}$ aryl or optionally substituted heterocycle;

R$^{10}$ is —OH, optionally substituted $C_{1-6}$ alkyl or optionally substituted $C_{6-10}$ aryl;

R$^{11}$ is —OH, optionally substituted $C_{1-6}$ alkyl or optionally substituted $C_{6-10}$ aryl;

R$^{12}$ is H or optionally substituted $C_{1-8}$ alkyl;

R$^{13}$ is H, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl or optionally substituted heterocycle;

R$^{14}$ is $C_{1-6}$ alkyl;

R$^{15}$ is $C_{1-6}$ alkyl; and each m is independently 1 or 2;

or an individual enantiomer or diastereoisomer thereof;
or a pharmaceutically acceptable salt of any of the foregoing;

provided that the compound is not:

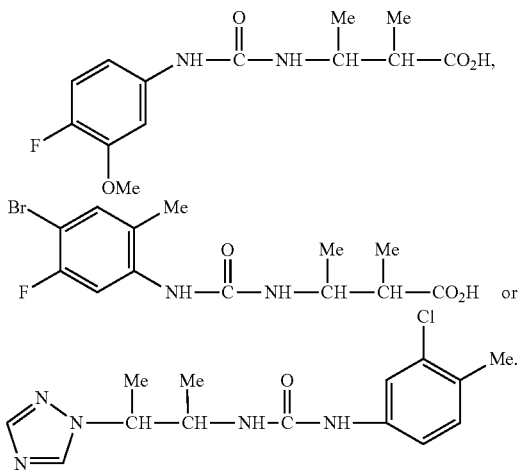

In embodiment (2a), there is provided the compound of embodiment (1a), wherein W is —COOH, sulfonate, sulfonic acid, phosphonate, phosphonic acid, phosphoric acid or $Het^1$, wherein $Het^1$ is tetrazole, imidazole, thiazole, oxazole, triazole, isoxazole, oxadiazole, thiadiazole, thiophene, pyrazole or pyrrole; preferably, W is —COOH.

In embodiment (3a), there is provided the compound of embodiment (1a) or (2a), wherein $R^1$ is unsubstituted $C_{2-6}$ alkyl.

In embodiment (4a), there is provided the compound of embodiment (3a), wherein $R^2$ is unsubstituted $C_{1-3}$ alkyl, preferably methyl.

In embodiment (5a), there is provided the compound of embodiment (4a), wherein $R^2$ is methyl, and $R^5$ is $C_{1-6}$ haloalkyl or halogen.

In embodiment (6a), there is provided the compound of any one of embodiments (1a) through (5a), wherein W is COOH.

In embodiment (7a), there is provided the compound of embodiment (1a), wherein each of $R^4$ and $R^6$ is H.

In embodiment (8a), there is provided the compound of embodiment (2a), wherein:
$R^1$ is unsubstituted $C_{2-6}$ alkyl;
$R^2$ is methyl;
$R^3$ is H or F;
$R^4$ is H;
$R^5$ is $C_{1-6}$ haloalkyl or halogen;
$R^6$ is H; and
$R^7$ is H or F.

In embodiment (9a), there is provided the compound of embodiment (1a), (2a) or (8a), wherein $R^1$ is unsubstituted ethyl, n-propyl, isopropyl, n-butyl, sec-butyl, isobutyl or tert-butyl.

In embodiment (10a), there is provided the compound of embodiment (1a), (2a) or (8a), wherein $R^1$ is isopropyl, n-butyl, sec-butyl, isobutyl or tert-butyl.

In embodiment (11a), there is provided the compound of embodiment (1a), (2a) or (8a), wherein $R^1$ is isopropyl or isobutyl, and $R^2$ is methyl.

In embodiment (12a), there is provided the compound of embodiment (1a), (2a) or (8a), wherein $R^1$ has the following structure:

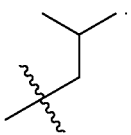 [SMILES: *CC(C)C]

In embodiment (13a), there is provided the compound of embodiment (1a) or (2a), wherein $R^1$ is unsubstituted benzyl; provided that $R^1$ and $R^2$ are not the same In embodiment (14a), there is provided the compound of embodiment (1a), wherein W is —COOH or —C(O)$OR^a$.

In embodiment (15a), there is provided the compound of embodiment (1a) or (14a), wherein W is —C(O)$OR^a$, preferably, $R^a$ is unsubstituted $C_{1-6}$ alkyl; optionally, the compound is a prodrug, wherein the ester is hydrolyzed in vivo to provide the corresponding carboxylic acid.

In embodiment (16a), there is provided the compound of embodiment (1a), (2a) or (8a), wherein W is unsubstituted $Het^1$, preferably triazole.

In embodiment (17a), there is provided the compound of embodiment (1a), (2a) or (8a), wherein $R^5$ is $C_{1-6}$ haloalkyl, F, Cl or Br; preferably, $R^5$ is —$CF_3$ or Br; most preferably, $R^5$ is Br.

In embodiment (18a), there is provided the compound of embodiment (1a) or (2a), wherein:
$R^1$ is unsubstituted ethyl, n-propyl, isopropyl, n-butyl, sec-butyl, isobutyl or tert-butyl;
$R^2$ is methyl;
$R^3$ is H;
$R^4$ is H;
$R^5$ is —$CF_3$, fluorine, chlorine or bromine;
$R^6$ is H; and
$R^7$ is H.

In embodiment (19a), there is provided the compound of embodiment (18a), wherein:
$R^1$ is unsubstituted n-propyl, isopropyl, n-butyl, sec-butyl, isobutyl or tert-butyl, preferably $R^1$ is isobutyl; and
$R^5$ is —$CF_3$ or bromine.

In embodiment (20a), there is provided the compound of embodiment (1a), (2a), (14a) or (15a), wherein:
$R^1$ is unsubstituted $C_{2-6}$ alkyl, preferably isopropyl or isobutyl;
$R^2$ is methyl;
$R^3$ is H or F;
$R^4$ is H;
$R^5$ is $C_{1-6}$ haloalkyl or halogen, preferably —$CF_3$ or bromine;
$R^6$ is H; and
$R^7$ is H or F.

In embodiment (21a), there is provided the compound of embodiment (1a), wherein the compound is a mixture of enantiomers, said mixture of enantiomers containing a single enantiomer of Formula 1-A and a single enantiomer of Formula 1-B; or a pharmaceutically acceptable salt thereof.

In embodiment (22a), there is provided the compound of embodiment (21a), wherein the mixture of enantiomers is a racemic mixture.

In embodiment (23a), there is provided the compound of any one of embodiments (1a) through (20a), wherein the compound is an individual enantiomer thereof; or a pharmaceutically acceptable salt thereof.

In embodiment (24a), there is provided the compound of embodiment (23a), wherein the individual enantiomer has the structure of Formula I-A:

Formula I-A

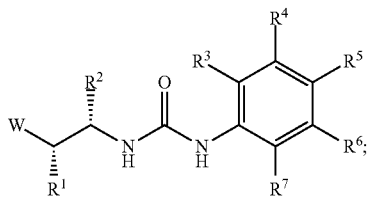

or a pharmaceutically acceptable salt thereof.

In embodiment (25a), there is provided the compound of embodiment (23a), wherein the individual enantiomer has the structure of Formula I-B:

Formula I-B

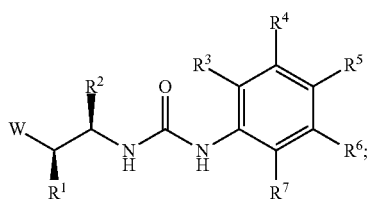

or a pharmaceutically acceptable salt thereof.

In embodiment (1b), there is provided a compound of Formula I-A, Formula 1-B, or a mixture thereof:

Formula I-C

Formula I-D wherein:
- W is —COOH, —C(O)OR$^a$, sulfonate, sulfonic acid, phosphonate, phosphonic acid, phosphoric acid, boronic acid or Het$^1$;
  wherein R$^a$ is optionally substituted C$_{1-6}$ alkyl, wherein said optional substituent is selected from the group consisting of —OH, halogen, —OC$_{1-8}$ alkyl and —(OC$_{1-8}$alkylene)$_q$-OC$_{1-8}$alkyl, wherein q is 1, 2, 3, 4, 5 or 6; and wherein Het$^1$ is a 5-membered aromatic heterocycle optionally substituted with one or more halogen, unsubstituted —C$_{1-6}$ alkyl, —C$_{1-6}$ haloalkyl, —OC$_{1-6}$alkyl, —(CH$_2$)$_{1-6}$OH, —(CH$_2$)$_{1-6}$NH$_2$, —(CH$_2$)$_{1-6}$NH(C$_{1-6}$alkyl) or —(CH$_2$)$_{1-6}$NR$^{14}$R$^{15}$,
- R$^1$ is optionally substituted C$_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{14}$R$^{15}$, urea, —COOH, —C(O)OC$_{1-6}$ alkyl, —C(O)NH$_2$, optionally substituted C$_{3-8}$ cycloalkyl, optionally substituted C$_{3-8}$ cycloalkenyl, optionally substituted C$_{6-10}$ aryl, and optionally substituted heterocycle;
- R$^2$ is optionally substituted C$_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{14}$R$^{15}$, urea, —COOH, —C(O)OC$_{1-6}$ alkyl, —C(O)NH$_2$, optionally substituted C$_{3-8}$ cycloalkyl, optionally substituted C$_{3-8}$ cycloalkenyl, optionally substituted C$_{6-10}$ aryl, and optionally substituted heterocycle;
- R$^3$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^9$, —S(O)$_m$R$^{10}$, —C(O)R$^{11}$, —SR$^{12}$ or —OR$^{12}$,
- R$^4$ is H, optionally substituted C$_{1-6}$ alkyl, C$_{1-6}$ haloalkyl, halogen, —S(O)$_m$R$^{10}$ or —C(O)R$^{11}$;
- R$^5$ is optionally substituted C$_{1-6}$ alkyl, C$_{1-6}$ haloalkyl, optionally substituted C$_m$ cycloalkyl, optionally substituted C$_{3-8}$ cycloalkenyl, optionally substituted C$_{6-10}$ aryl, optionally substituted heterocycle, halogen, —S(O)$_m$R$^{10}$, —C(O)R$^{11}$, —SR$^{13}$ or —OR$^{13}$,
- R$^6$ is H, optionally substituted C$_{1-6}$ alkyl, C$_{1-6}$ haloalkyl, halogen, —S(O)$_m$R$^{10}$ or —C(O)R$^{11}$;
- R$^7$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^8$, —S(O)$_m$R$^{10}$, —C(O)R$^{11}$, —SR$^{12}$ or —OR$^{12}$,
- R$^8$ is H, optionally substituted C$_{1-6}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
- R$^9$ is H, optionally substituted C$_{1-6}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
- R$^{10}$ is —OH, optionally substituted C$_{1-6}$ alkyl or optionally substituted C$_{6-10}$ aryl;
- R$^{11}$ is —OH, optionally substituted C$_{1-6}$ alkyl or optionally substituted C$_{6-10}$ aryl;
- R$^{12}$ is H or optionally substituted C$_{1-8}$ alkyl;
- R$^{13}$ is H, optionally substituted C$_{1-8}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
- R$^{14}$ is C$_{1-6}$ alkyl;
- R$^{15}$ is C$_{1-6}$ alkyl; and
- each m is independently 1 or 2;

or an individual enantiomer or diastereoisomer thereof; or a pharmaceutically acceptable salt of any of the foregoing;

provided that the compound is not:

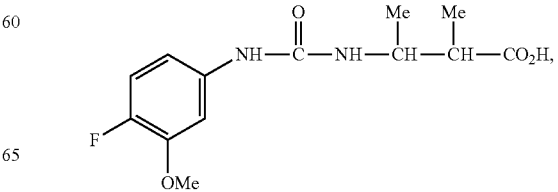

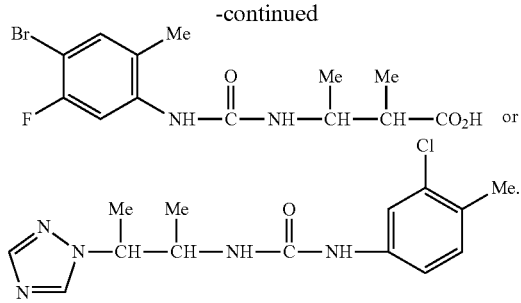

In embodiment (2b), there is provided the compound of embodiment (1b), wherein W is —COOH, sulfonate, sulfonic acid, phosphonate, phosphonic acid, phosphoric acid or $Het^1$, wherein $Het^1$ is tetrazole, imidazole, thiazole, oxazole, triazole, isoxazole, oxadiazole, thiadiazole, thiophene, pyrazole or pyrrole; preferably, W is —COOH.

In embodiment (3b), there is provided the compound of embodiment (1b) or (2b), wherein $R^1$ is unsubstituted $C_{2-6}$ alkyl.

In embodiment (4b), there is provided the compound of embodiment (3b), wherein $R^2$ is unsubstituted $C_{1-3}$ alkyl, preferably methyl.

In embodiment (5b), there is provided the compound of embodiment (4b), wherein $R^2$ is methyl, and $R^5$ is $C_{1-6}$ haloalkyl or halogen.

In embodiment (6b), there is provided the compound of any one of embodiments (1b) through (5b), wherein W is COOH.

In embodiment (7b), there is provided the compound of embodiment (1b), wherein each of $R^4$ and $R^6$ is H.

In embodiment (8b), there is provided the compound of embodiment (2b), wherein:
$R^1$ is unsubstituted $C_{2-6}$ alkyl;
$R^2$ is methyl;
$R^3$ is H or F;
$R^4$ is H;
$R^5$ is $C_{1-6}$ haloalkyl or halogen;
$R^6$ is H; and
$R^7$ is H or F.

In embodiment (9b), there is provided the compound of embodiment (1b), (2b) or (8b), wherein $R^1$ is unsubstituted ethyl, n-propyl, isopropyl, n-butyl, sec-butyl, isobutyl or tert-butyl.

In embodiment (10b), there is provided the compound of embodiment (1b), (2b) or (8b), wherein $R^1$ is isopropyl, n-butyl, sec-butyl, isobutyl or tert-butyl.

In embodiment (11b), there is provided the compound of embodiment (1b), (2b) or (8b), wherein $R^1$ is isopropyl or isobutyl, and $R^2$ is methyl.

In embodiment (12b), there is provided the compound of embodiment (1b), (2b) or (8b), wherein $R^1$ has the following structure:

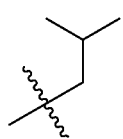

In embodiment (13b), there is provided the compound of embodiment (1b) or (2b), wherein $R^1$ is unsubstituted benzyl; provided that $R^1$ and $R^2$ are not the same.

In embodiment (14b), there is provided the compound of embodiment (1b), wherein W is —COOH or —C(O)$OR^a$.

In embodiment (15b), there is provided the compound of embodiment (1b) or (14b), wherein W is —C(O)$OR^a$, preferably, $R^a$ is unsubstituted $C_{1-6}$ alkyl; optionally, the compound is a prodrug, wherein the ester is hydrolyzed in vivo to provide the corresponding carboxylic acid.

In embodiment (16b), there is provided the compound of embodiment (1b), (2b) or (8b), wherein W is unsubstituted $Het^1$, preferably triazole.

In embodiment (17b), there is provided the compound of embodiment (1b), (2b) or (8b), wherein $R^5$ is $C_{1-6}$ haloalkyl, F, Cl or Br; preferably, $R^5$ is —$CF_3$ or Br; most preferably, $R^5$ is Br.

In embodiment (18b), there is provided the compound of embodiment (1b) or (2b), wherein:
$R^1$ is unsubstituted ethyl, n-propyl, isopropyl, n-butyl, sec-butyl, isobutyl or tert-butyl;
$R^2$ is methyl;
$R^3$ is H;
$R^4$ is H;
$R^5$ is —$CF_3$, fluorine, chlorine or bromine;
$R^6$ is H; and
$R^7$ is H.

In embodiment (19b), there is provided the compound of embodiment (18b), wherein:
$R^1$ is unsubstituted n-propyl, isopropyl, n-butyl, sec-butyl, isobutyl or tert-butyl, preferably $R^1$ is isobutyl; and
$R^5$ is —$CF_3$ or bromine.

In embodiment (20b), there is provided the compound of embodiment (1b), (2b) (14b) or (15b), wherein:
$R^1$ is unsubstituted $C_{2-6}$ alkyl, preferably isopropyl or isobutyl;
$R^2$ is methyl;
$R^3$ is H or F;
$R^4$ is H;
$R^5$ is $C_{1-6}$ haloalkyl or halogen, preferably —$CF_3$ or bromine;
$R^6$ is H; and
$R^7$ is H or F.

In embodiment (21b), there is provided the compound of embodiment (1b), wherein the compound is a mixture of enantiomers, said mixture of enantiomers contaiing a single enantiomer of Formula 1-C and single enantiomer of Formula 1-D; or a pharmaceutically acceptable salt thereof.

In embodiment (22b), there is provided the compound of embodiment (21b), wherein the mixture of enantiomers is a racemic mixture.

In embodiment (23b), there is provided the compound of any one of embodiments (1b) through (20b), wherein the compound is an individual enantiomer thereof; or a pharmaceutically acceptable salt thereof.

In embodiment (24b), there is provided the compound of embodiment (23b), wherein the individual enantiomer has the structure of Formula I-C:

Formula I-C

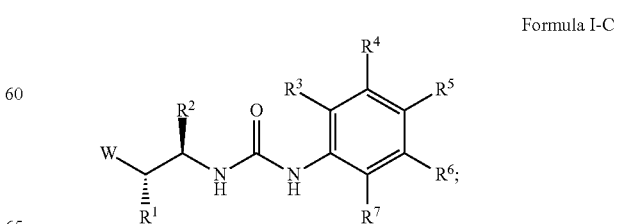

or a pharmaceutically acceptable salt thereof.

In embodiment (25b), there is provided the compound of embodiment (23b), wherein the individual enantiomer has the structure of Formula I-D:

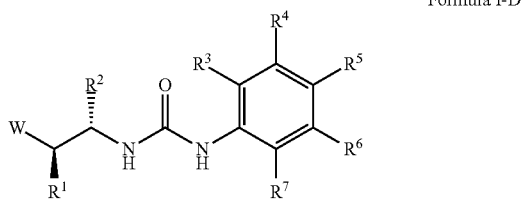

Formula I-D or a pharmaceutically acceptable salt thereof.

In embodiment (1c), there is provided a pharmaceutical composition comprising a compound of any one of embodiments (1) through (40), (1a) through (25a) and (1b) through (25b), or a pharmaceutically acceptable salt thereof; and a pharmaceutically acceptable excipient.

In embodiment (2c), there is provided a pharmaceutical composition comprising a therapeutically effective amount of a compound of any one of embodiments (1) through (40), (1a) through (25a) and (1b) through (25b), or a pharmaceutically acceptable salt thereof; and a pharmaceutically acceptable excipient.

In embodiment (3c), there is provided the pharmaceutical composition of embodiment (1c) or (2c), wherein the pharmaceutically acceptable excipient is an ophthalmically acceptable excipient.

In embodiment (1d), there is provided a method of treating a disease or condition associated with formyl peptide receptor (FPR) modulation in a subject in need thereof, the method comprising administering to the subject (a) a therapeutically effective amount of a compound of any one of embodiments (1) through (40), (1a) through (25a) and (1b) through (25b), or a pharmaceutically acceptable salt thereof; or (b) a pharmaceutical composition of embodiment (1c), (2c) or (3c), thereby treating the disease or condition.

In embodiment (2d), there is provided the method of embodiment (1d), wherein the disease or condition is an ocular inflammatory disease or condition.

In embodiment (3d), there is provided the method of embodiment (1d) or (2d), wherein the condition is dry eye, and wherein the method treats the condition.

In embodiment (4d), there is provided the method of embodiment (1d) or (2d), wherein the condition is suppressed tear production, and the method results in the enhancement of tear production.

In embodiment (5d), there is provided the method of embodiment (4d), wherein the suppressed tear production is due to ocular inflammation associated with keratoconjunctivitis sicca (dry eye disease).

In embodiment (6d), there is provided the method of embodiment (1d) or (2d), wherein the disease or condition is a post-surgical inflammation, and the method reduces the inflammation.

In embodiment (7d), there is provided the method of embodiment (6d), wherein the post-surgical inflammation is post-cataract surgical inflammation.

In embodiment (8d), there is provided the method of embodiment (1d) or (6d), wherein the disease or condition is a corneal wound, such as a post-surgical corneal wound.

In embodiment (9d), there is provided the method of embodiment (1d), wherein the disease or condition is a dermal inflammatory disease or condition.

In embodiment (10d), there is provided the method of embodiment (1d) or (9d), wherein the method reduces the dermatological inflammation.

In embodiment (11d), there is provided the method of embodiment (1d) or (9d), wherein the disease or condition is psoriasis.

In embodiment (12d), there is provided the method of embodiment (1d) or (9d), wherein the disease or condition is rosacea.

In embodiment (13d), there is provided the method of embodiment (1d) or (9d), wherein the disease or condition is a dermal wound.

In embodiment (14d), there is provided the method of embodiment (1d), wherein the disease or condition is a gastrointestinal disease or condition.

In embodiment (15d), there is provided the method of embodiment (1d) or (14d), wherein the disease or condition is an inflammatory bowel disease, such as Crohn's disease.

In embodiment (16d), there is provided the method of embodiment (1d) or (14d), wherein the disease or condition is ulcerative colitis.

In embodiment (17d), there is provided the method of embodiment (1d), wherein the compound or pharmaceutical composition is administered to the subject topically, orally, systemically or via an implant.

In embodiment (18d), there is provided the method of any one of embodiments (1d) through (17d), wherein the subject is a human.

In embodiment (1e), there is provided a method of selectively modulating an FPR1 receptor relative to an FPR2 receptor in a recipient, the method comprising administering a compound of any one of embodiments (1) through (40), (1a) through (25a) and (1b) through (25b), or a pharmaceutically acceptable salt thereof, to the recipient, wherein the compound exhibits at least 2-fold selectivity for FPR1 relative to FPR2, and wherein the selectivity is based on the ratio of the $EC_{50}$ for agonizing FPR2 to the $EC_{50}$ for agonizing FPR1 as measured in an in vitro, ex vitro and/or in vivo assay; preferably, W is —COOH.

In embodiment (2e), there is provided a method of embodiment (1e), wherein the recipient is a mammalian subject.

In embodiment (3e), there is provided a method of embodiment (2e), wherein the subject is a human.

In embodiment (4e), there is provided a method of embodiment (1e), wherein the recipient is a cell or tissue.

In embodiment (5e), there is provided a method of embodiment (4e), wherein the compound is administered to the cell or tissue recipient in vitro.

In embodiment (6e), there is provided a method of embodiment (4e), wherein the compound is administered to the cell or tissue recipient ex vivo.

In embodiment (7e), there is provided the method of embodiment (1e), wherein the recipient is an in vitro FPR receptor assay system.

In embodiment (8e), there is provided the method of any one of embodiments (1e) through (7e), wherein the compound exhibits at least 5-fold selectivity for FPR1 compared to FPR2.

In embodiment (9e), there is provided the method of any one of embodiments (1e) through (7e), wherein the compound exhibits at least 10-fold selectivity for FPR1 compared to FPR2.

In embodiment (10e), there is provided the method of any one of embodiments (1e) through (7e), wherein the compound exhibits at least 20-fold selectivity for FPR1 compared to FPR2.

In embodiment (11e), there is provided the method of any one of embodiments (1e) through (7e), wherein the compound exhibits at least 50-fold selectivity for FPR1 compared to FPR2.

In embodiment (12e), there is provided the method of any one of embodiments (1e) through (7e), wherein the compound exhibits at least 100-fold selectivity for FPR1 compared to FPR2.

In embodiment (13e), there is provided the method of any one of embodiments (1e) through (7e), wherein the compound exhibits at least 200-fold selectivity for FPR1 compared to FPR2.

In embodiment (14e), there is provided the method of embodiment (1e), wherein the compound is:

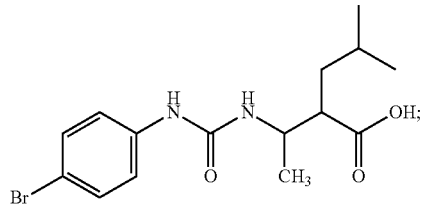 [SMILES: CC(C)CC(C(=O)O)C(C)NC(=O)Nc1ccc(Br)cc1]

or a mixture of two or more diastereomers thereof;
or a mixture of enantiomers thereof;
or an individual enantiomer or diastereoisomer thereof;
or a pharmaceutically acceptable salt of any of the foregoing.

In embodiment (15e), there is provided the method of embodiment (1e), wherein the compound is selected from the group consisting of:

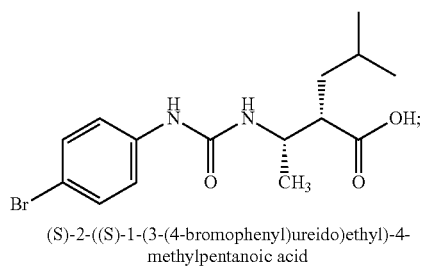
(S)-2-((S)-1-(3-(4-bromophenyl)ureido)ethyl)-4-methylpentanoic acid

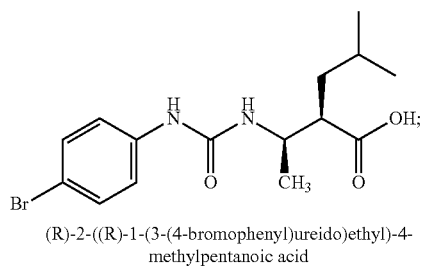
(R)-2-((R)-1-(3-(4-bromophenyl)ureido)ethyl)-4-methylpentanoic acid

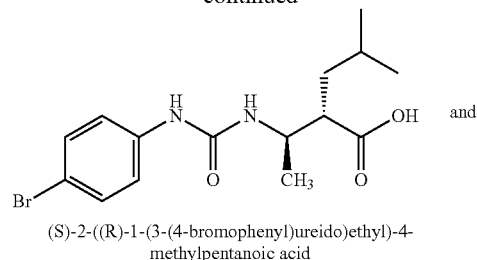
(S)-2-((R)-1-(3-(4-bromophenyl)ureido)ethyl)-4-methylpentanoic acid

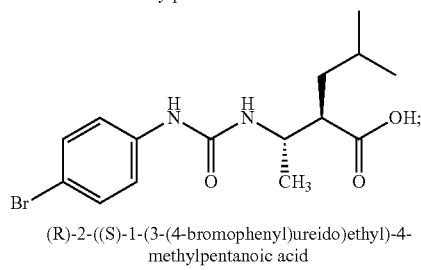
(R)-2-((S)-1-(3-(4-bromophenyl)ureido)ethyl)-4-methylpentanoic acid and a mixture of any two or more of the foregoing; and pharmaceutically acceptable salts thereof.

In embodiment (16e), there is provided the method of embodiment (1e), wherein the compound is Compound 102, or a pharmaceutically acceptable salt thereof.

In embodiment (17e), there is provided the method of embodiment (1e), wherein the compound is Compound 103, or a pharmaceutically acceptable salt thereof.

In embodiment (18e), there is provided the method of embodiment (1e), wherein the compound is Compound 104, or a pharmaceutically acceptable salt thereof.

In embodiment (19e), there is provided the method of embodiment (1e), wherein the compound is Compound 105, or a pharmaceutically acceptable salt thereof.

In embodiment (20e), there is provided the method of embodiment (1e), wherein the compound is Compound 106, or a pharmaceutically acceptable salt thereof.

In embodiment (21e), there is provided the method of embodiment (1e), wherein the compound is Compound 107, or a pharmaceutically acceptable salt thereof.

In embodiment (A), there is provided a method of screening for a substance that modulates an FPR receptor, the method comprising:
a) contacting an FPR receptor with a test substance,
b) determining the ability of the test substance to modulate the FPR receptor, and
c) comparing the ability of the test substance to modulate the FPR receptor with the ability of a compound of any one of embodiments (1) through (40), (1a) through (25a) and (1b) through (25b) to modulate an FPR receptor of the same subtype(s); preferably W is —COOH.

In embodiment (B), there is provided the method of embodiment (A), wherein the FPR receptor is selected from a group of FPR receptor subtypes consisting of:
(i) FPR1;
(ii) FPR1 and FPR2;
(iii) FPR1 and FPR3; and
(iv) FPR1, FPR2 and FPR3.

In embodiment (C), there is provided the method of embodiment (A) or (B), wherein the compound serves as a control.

In embodiment (D), there is provided the method of any one of embodiments (A) through (C), wherein the method identifies the substance as an FPR modulator.

In embodiment (E), there is provided the method of any one of embodiments (A) through (D), wherein the determining of the ability of the test substance to modulate the FPR receptor comprises determining an increase or decrease in the FPR receptor activity level.

In embodiment (F), there is provided the method of embodiment (E), wherein the increase or decrease in the FPR receptor activity level indicates that the substance is an FPR receptor agonist or antagonist, respectively.

In embodiment (G), there is provided the method of any one of embodiments (A) through (F), wherein the method indicates that the substance is a selective FPR1 receptor subtype agonist.

In embodiment (H), there is provided the method of any one of embodiments (A) through (F), wherein the method indicates that the substance is an FPR1 receptor subtype agonist and an FPR2 receptor subtype agonist.

In embodiment (I), there is provided the method of any one of embodiments (A) through (H), wherein the compound is selected from any one of embodiments (1) through (40), (1a) through (25a) and (1b) through (25b); provided that W is not —C(O)OR$^a$.

In embodiment (J), there is provided the method of any one of embodiments (A) through (I), wherein the compound is:

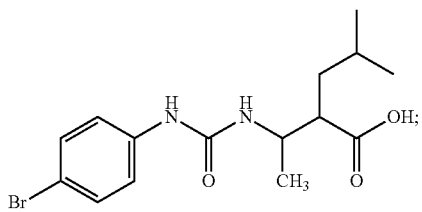 [SMILES: CC(C)CC(C(=O)O)C(C)NC(=O)Nc1ccc(Br)cc1]

or a mixture of two or more diastereomers thereof;
or a mixture of enantiomers thereof;
or an individual enantiomer or diastereoisomer thereof;
or a pharmaceutically acceptable salt of any of the foregoing;

In embodiment (K), there is provided the method of any one of embodiments (A) through (I), wherein the compound is selected from the group consisting of:

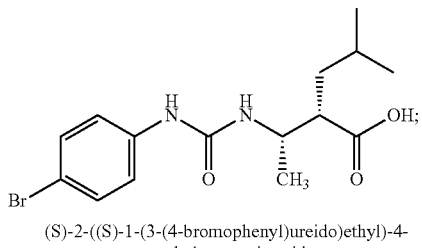

(S)-2-((S)-1-(3-(4-bromophenyl)ureido)ethyl)-4-methylpentanoic acid

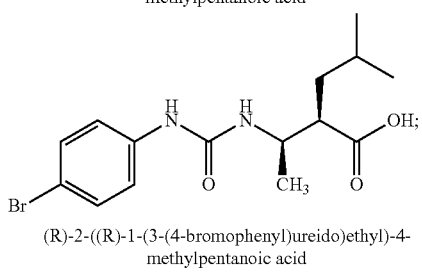

(R)-2-((R)-1-(3-(4-bromophenyl)ureido)ethyl)-4-methylpentanoic acid

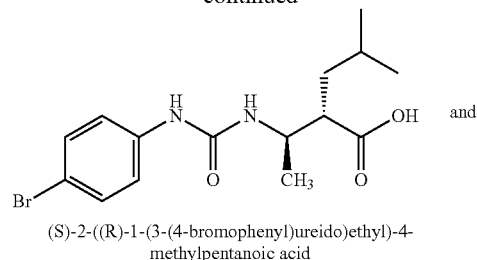

(S)-2-((R)-1-(3-(4-bromophenyl)ureido)ethyl)-4-methylpentanoic acid

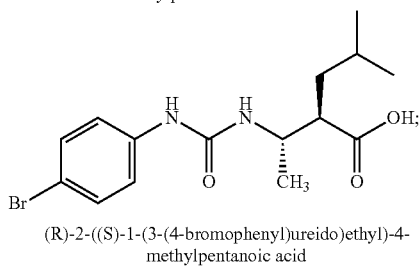

(R)-2-((S)-1-(3-(4-bromophenyl)ureido)ethyl)-4-methylpentanoic acid and a mixture of any two or more of the foregoing;
and pharmaceutically acceptable salts thereof.

In embodiment L, there is provided the method of any one of embodiments A through H, wherein the compound is Compound 102, or a pharmaceutically acceptable salt thereof.

In embodiment M, there is provided the method of any one of embodiments A through H, wherein the compound is Compound 103, or a pharmaceutically acceptable salt thereof.

In embodiment N, there is provided the method of any one of embodiments A through H, wherein the compound is Compound 104, or a pharmaceutically acceptable salt thereof.

In embodiment 0, there is provided the method of any one of embodiments A through H, wherein the compound is Compound 105, or a pharmaceutically acceptable salt thereof.

In embodiment P, there is provided the method of any one of embodiments A through H, wherein the compound is Compound 106, or a pharmaceutically acceptable salt thereof.

In embodiment Q, there is provided the method of any one of embodiments A through H, wherein the compound is Compound 107, or a pharmaceutically acceptable salt thereof.

In embodiment R, there is provided the use of a compound of any one of embodiments (1) through (40), (1a) through (25a) and (1b) through (25b) in a method of identifying a substance having FPR1 receptor modulatory activity.

In embodiment S, there is provided the use of embodiment R, wherein the FPR1 receptor modulatory activity is FPR1 receptor agonist activity.

In embodiment T, there is provided the use of embodiment R or S, wherein the substance is identified as having selective FPR1 agonist activity relative to FPR2.

In embodiment U, there is provided the use of embodiment R, S or T, wherein the method is selected from any one of embodiments (A) through (Q).

In embodiment (V), there is provided a use of a compound of any one of embodiments (1) through (40), (1a) through (25a) and (1b) through (25b) in identifying a biochemical and/or pharmacological effect(s) of agonizing an FPR1 receptor in a cell or tissue; preferably, W is —COOH.

The present invention also concerns processes for preparing compounds of Formula I.

Synthetic Schemes 1 and the Examples set forth below illustrate how the compounds according to the invention can be made, and provide details of certain specific chemical transformations. The Examples are for illustrative purposes only and are not intended, nor should they be construed, as limiting the invention in any manner. Those skilled in the art will be able to routinely modify and/or adapt the Scheme or Examples to synthesize any compound of the invention that falls within the scope of Formula I, I-A, I-B, I-C or I-D, and will appreciate that variations and modifications of the Examples can be made without exceeding the spirit or scope of the invention.

EXAMPLES

All reagents, solvents and catalysts for which the synthesis is not described are purchased from chemical vendors such as 3B Scientific, Sigma Aldrich, Fluke, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates were prepared according to published procedures.

Compound names were generated with ACDLab version 12.5; some intermediate and reagent names used in the Examples were generated with software such as Chem Bio Draw Ultra version 12.0, ACDLab version 12.5 or Auto Nom 2000 from MDL ISIS Draw 2.5 SP1.

In general, characterization of the compounds was performed using NMR spectroscopy. NMR spectra were acquired on a 300 or 600 MHz Varian NMR spectrometer at room temperature. Chemical shifts are given in ppm referenced either to internal TMS or to the solvent signal.

Usually, the compounds of the invention were purified by medium pressure liquid chromatography, unless noted otherwise.

The following abbreviations are used herein:
Ac acetate
$CD_3OD$ deuterated methanol
DCM dichloromethane
DEA diethylamine
$Et_3N$ triethylamine
EtOAc ethyl acetate
$H_2$ hydrogen gas
$HCO_2H$ formic acid
HPLC high performance liquid chromatography
IA immobilized cellulose/amylose chiral stationary phase
MeOH methanol
MPLC medium pressure liquid chromatography
$Na_2SO_4$ sodium sulfate
Pd/C palladium on carbon
SFC supercritical fluid chromatography
THF tertahydrofuran
TMS tetramethylsilane

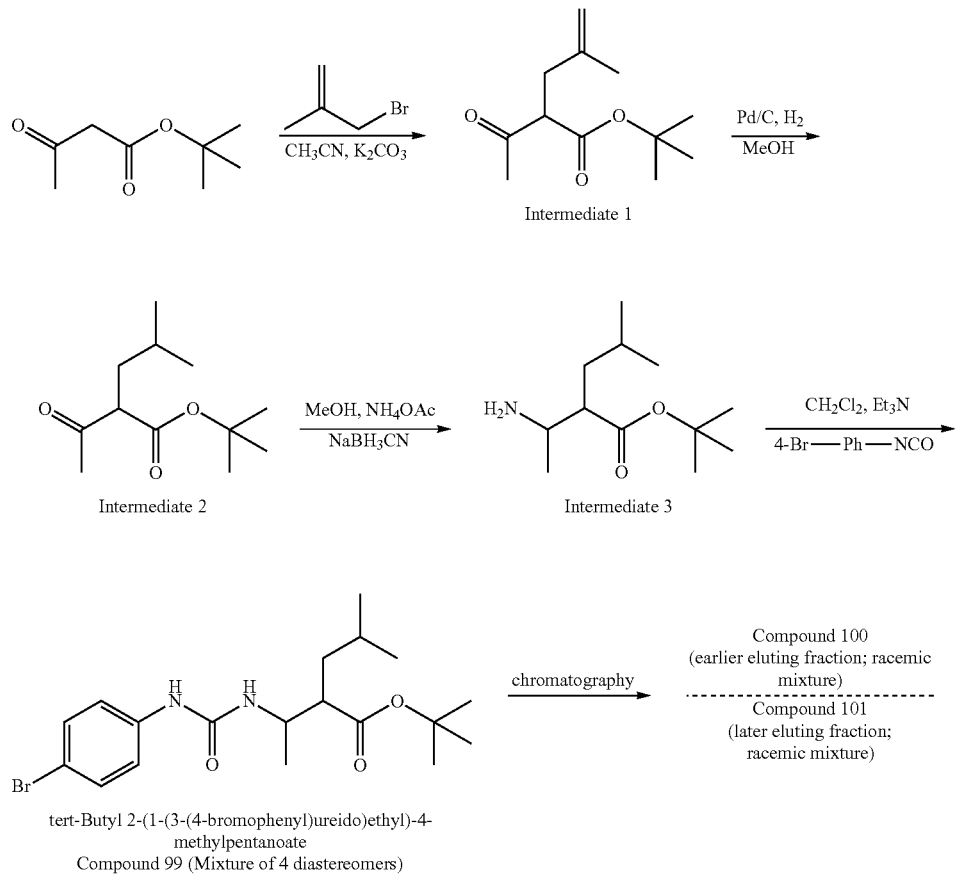

Scheme 1. General strategy for the synthesis of compounds of the invention.

tert-Butyl 2-(1-(3-(4-bromophenyl)ureido)ethyl)-4-methylpentanoate
Compound 99 (Mixture of 4 diastereomers)

-continued
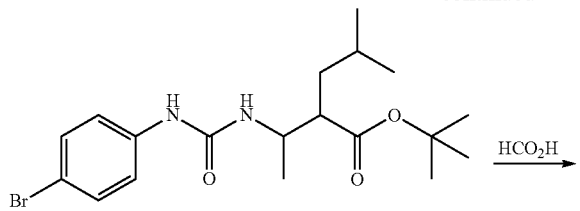
Compound 100
(earlier eluting racemic mixture)
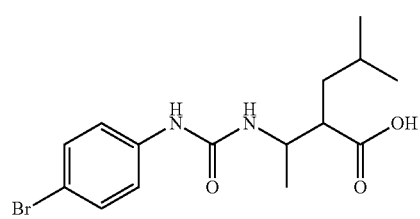
Compound 102
(racemic mixture)
HPLC Chiral Resolution
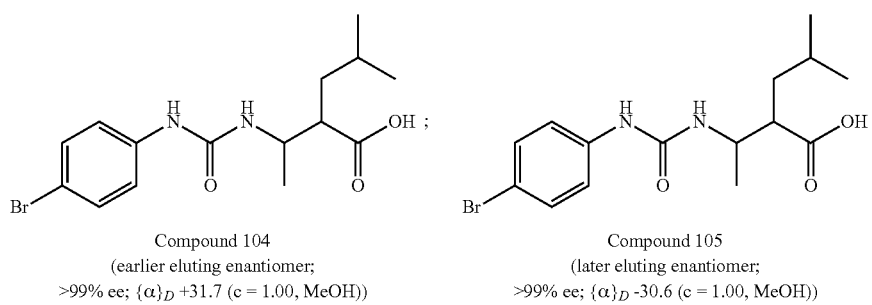
Compound 104
(earlier eluting enantiomer;
>99% ee; $\{\alpha\}_D$ +31.7 (c = 1.00, MeOH))
Compound 105
(later eluting enantiomer;
>99% ee; $\{\alpha\}_D$ -30.6 (c = 1.00, MeOH))
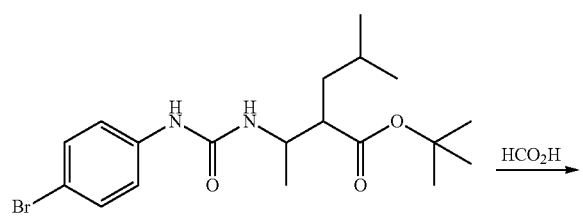
Compound 101
(later eluting racemic mixture)
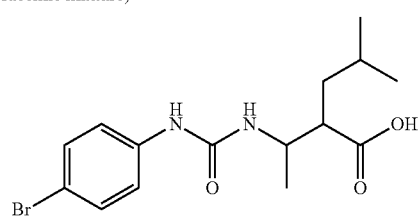
Compound 103
(racemic mixture)
HPLC Chiral Resolution

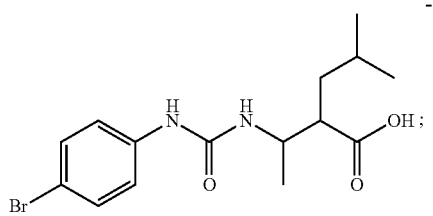

Compound 106
(earlier eluting enantiomer;
98% ee; {α}$_D$ -4.3 (c = 1.00, MeOH))

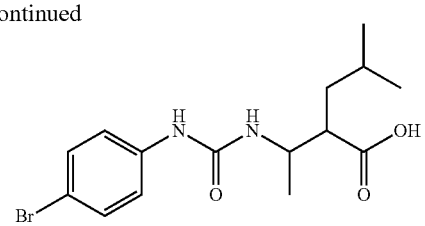

Compound 107
(later eluting enantiomer;
>99% ee; {α}$_D$ +4.2 (c = 1.00, MeOH))

Intermediate 1 tert-Butyl 2-acetyl-4-methylpent-4-enoate

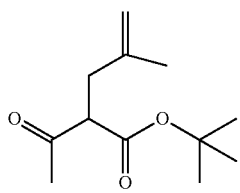

To a solution of tert-butyl acetoacetate (5.47 g, 34.6 mmol) and 100 mL of anhydrous acetonitrile at 25° C. under argon was added K$_2$OC$_3$ (4.77 g, 34.6 mmol), and 3-bromo-2-methyl-prop-1-ene (6.62 g, 49.1 mmol). The resulting mixture was stirred at 25° C. for 4 days. The mixture was filtered through a Celite® pad and concentrated under reduced pressure. The resulting product was purified by medium pressure liquid chromatography on silica gel using ethyl acetate:hexanes (1:9) to yield Intermediate 1 as a clear oil. $^1$H NMR (CDCl$_3$, 300 MHz) δ: 4.76 (s, 1H), 4.68 (s, 1H), 3.54 (t, J=7.6 Hz, 1H), 2.50 (d, J=7.6 Hz, 2H), 2.21 (s, 3H), 1.72 (s, 3H), 1.44 (s, 9H).

Intermediate 2 tert-Butyl 2-acetyl-4-methylpentanoate

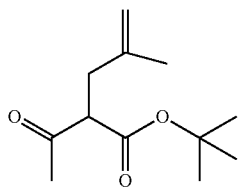

To a solution of Intermediate 1 (5.28 g, 24.9 mmol) and 125 mL of methanol were added 10% Pd/C (530 mg) and a hydrogen balloon. The resulting mixture was stirred at 25° C. for 12 hours. The mixture was filtered through a Celite® pad and concentrated under reduced to yield Intermediate 2 as an oil. $^1$H NMR (CDCl$_3$, 300 MHz) δ: 3.38 (dd, J=8.1, 6.6 Hz, 1H), 2.20 (s, 3H), 1.57-1.80 (m, 3H), 1.45 (s, 9H), 0.91 (d, J=1.8 Hz, 3H), 0.89 (d, J=1.5 Hz, 3H).

Intermediate 3 tert-Butyl 2-(1-aminoethyl)-4-methylpentanoate

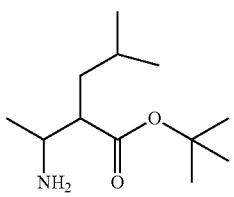

To a solution of Intermediate 2 (4.34 g, 20.3 mmol) and 100 mL of methanol at 25° C. under argon was added sodium cyanoborohydride (1.48 g, 23.5 mmol) and ammonium acetate (39.5 g, 507 mmol). The resulting mixture was stirred at 25° C. for 1 hour. The mixture was diluted with ethyl acetate (200 mL), and washed with water, brine, dried over Na$_2$SO$_4$, filtered, and the filtrate was concentrated under reduced pressure to yield Intermediate 3 as a clear oil. $^1$H NMR (CDCl$_3$, 300 MHz) δ: 3.46 (td, J=7.0, 4.4 Hz, 1H), 2.61 (dt, J=9.4, 4.5 Hz, 1H), 1.61-1.71 (m, 2H), 1.48 (s, 9H), 1.31-1.26 (m, 1H), 1.21-1.27 (m, 3H), 0.93 (d, J=5.6 Hz, 6H).

Compound 99 tert-Butyl 2-(1-(3-(4-bromophenyl)ureidoethyl-4-methylpentanoate

Compound 99

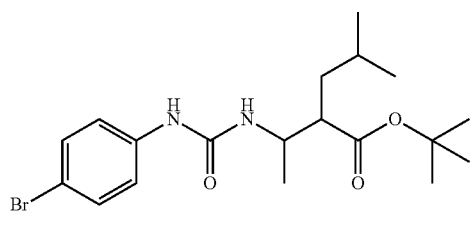

(Mixture of 4 diastereomers)

To a solution of Intermediate 3 (2.01 g, 9.36 mmol) and 30 mL of methylene chloride at 25° C. was added 4-bromophenyl isocyanate (1.84 g, 9.36 mmol) and triethylamine (1.95 mL, 14.0 mmol). The resulting mixture was stirred at 25° C. for 12 hours. The mixture was concentrated to a residue containing tert-butyl 2-(1-(3-(4-bromophenyl)

ureido)ethyl)-4-methylpentanoate as a mixture of four diastereomers (Compound 99).

Compounds 100 and 101 tert-Butyl 241-(3-(4-bromophenyl)ureido)ethyl)-4-methylpentanoate

The residue containing the mixture of the 4 diastereomers (Compound 99) was purified by medium pressure liquid chromatography on silica gel using ethyl acetate:hexanes (15:85).

Earlier eluting fractions were collected and dried under reduced pressure to obtain tert-butyl 2-(1-(3-(4-bromophenyl)ureido)ethyl)-4-methylpentanoate (Compound 100, racemic mixture) as white solid. $^1$H NMR (CD$_3$OD, 300 MHz) δ: 7.67-7.71 (m, 2H), 7.58-7.65 (m, 2H), 6.48 (d, J=9.4 Hz, NH), 4.27-4.36 (m, 1H), 2.81 (dt, J=9.7, 5.1 Hz, 1H), 1.88-2.00 (m, 2H), 1.59-1.65 (m, 1H), 1.49 (d, J=6.5 Hz, 3H), 1.24-1.28 (m, 6H).

Compound 100

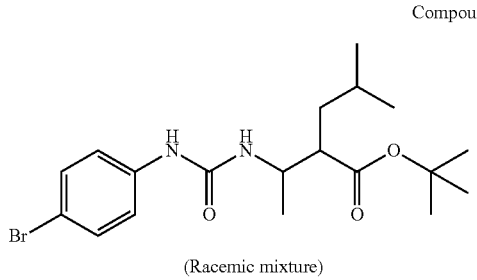

(Racemic mixture)

Later eluting fractions were collected and dried under reduced pressure to yield tert-butyl 2-(1-(3-(4-bromophenyl)ureido)ethyl)-4-methylpentanoate (Compound 101, racemic mixture) as a white solid. $^1$H NMR (CD$_3$OD, 300 MHz) δ: 7.35-7.40 (m, 2H), 7.26-7.32 (m, 2H), 5.97 (d, J=8.8 Hz, NH), 3.92-4.01 (m, 1H), 2.46 (ddd, J=11.0, 7.5, 3.8 Hz, 1H), 1.64 (ddd, J=13.2, 10.9, 4.7 Hz, 1H), 1.55 (ddd, J=9.1, 4.4, 2.3 Hz, 1H), 1.46-1.47 (m, 9H), 1.30 (ddd, J=13.4, 9.5, 3.5 Hz, 1H), 1.16 (d, J=7.0 Hz, 3H), 0.92 (d, J=1.8 Hz, 3H), 0.91 (d, J=1.8 Hz, 3H).

Compound 101

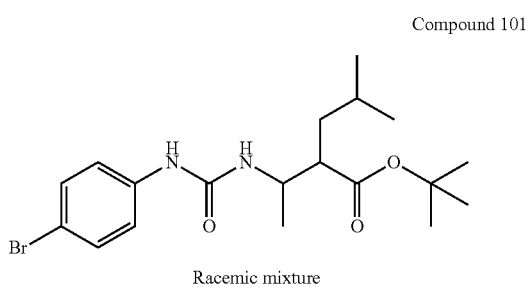 [SMILES: CC(C)CC(C(=O)OC(C)(C)C)C(C)NC(=O)Nc1ccc(Br)cc1]

Racemic mixture

Compound 102

2-(1-(3-(4-bromophenyl)ureido)ethyl)-4-methylpentanoic acid

Compound 102

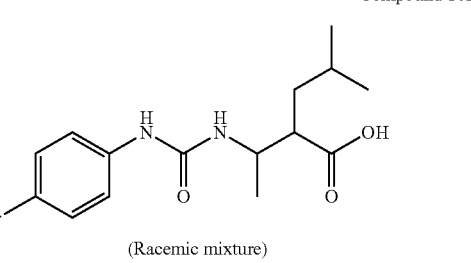

(Racemic mixture)

A solution of Compound 100 (racemic mixture; 701 mg, 1.70 mmol) and 15 mL of formic acid was stirred at 25° C. for 12 hours. The resulting reaction was quenched with water (10 mL), and the product was extracted with EtOAc. The organic layer was washed with water, brine, dried over Na$_2$SO$_4$, filtered, and concentrated under reduced pressure. The residue was rinsed four times with acetone:hexanes (2:98) to yield Compound 102 (racemic mixture) as a white solid. $^1$H NMR (CD$_3$OD, 300 MHz) δ: 7.33-7.37 (m, 2H), 7.28-7.31 (m, 2H), 4.03 (br. s., 1H), 2.59 (d, J=4.1 Hz, 1H), 1.58-1.67 (m, 2H), 1.31-1.40 (m, 1H), 1.14-1.22 (m, 3H), 0.93 (d, J=2.9 Hz, 6H).

Compound 103

2-(1-(3-(4-bromophenyl)ureido)ethyl)-4-methylpentanoic acid

Compound 103

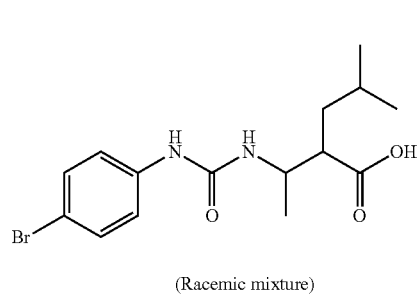

(Racemic mixture)

Compound 103 was prepared according to the procedure described for Compound 102, except that Compound 101 was used as the starting material. Compound 103 (racemic mixture) was obtained as an off-white solid. $^1$H NMR (CD$_3$OD, 300 MHz) δ: 7.33-7.40 (m, 2H), 7.29 (d, J=8.8 Hz, 2H), 3.96-4.06 (m, 1H), 2.54 (br. s., 1H), 1.64-1.71 (m, 1H), 1.56-1.63 (m, 1H), 1.28-1.36 (m, 1H), 1.18 (d, J=7.0 Hz, 3H), 0.91-0.95 (m, 6H).

Compound 104 (Enantiomer) and Compound 105 (Enantiomer)

2-(1-(3-(4-bromophenyl)ureido)ethyl)-4-methylpentanoic acid

Compound 102 (racemic mixture) was subjected to preparative HPLC SFC separation: Chiralpak IA (2×25 cm), 20% ethanol (0.1% DEA)/CO$_2$, 100 bar, 65 mL/min, 254 nm, inj vol.: 1 mL, 15 mg/mL, (1:1) methanol:DCM to give Compound 104 (enantiomer present in the earlier eluting fraction) and Compound 105 (enantiomer present in the late eluting fraction).

Compound 104 (>99% ee): white solid; [α]p=+31.7 (c=1.00, MeOH), $^1$H NMR (CD$_3$OD, 600 MHz) δ: 7.33-7.36 (m, 2H), 7.29-7.32 (m, 2H), 3.86 (br s., 1H), 3.04 (m, 1H), 1.64 (br. s., 1H), 1.30 (m, 3H), 1.20 (d, J=5.3 Hz, 2H), 0.93 (d, J=5.3 Hz, 3H), 0.90 (d, J=5.9 Hz, 3H).

Compound 105 (>99% ee): yellow solid, [α]$_D$=−30.6 (c=1.00, MeOH), $^1$H NMR (CD$_3$OD, 600 MHz) δ: 7.33-7.36 (m, 2H), 7.28-7.32 (m, 2H), 3.87 (br s., 1H), 3.04 (m, 1H), 1.64 (br s., 1H), 1.30 (m, 3H), 1.20 (br s, 2H), 0.92 (s, 3H), 0.90 (s, 3H).

Compounds 106 (Enantiomer) and Compound 107 (Enantiomer)

2-(1-(3-(4-bromophenyl)ureido)ethyl)-4-methylpentanoic acid

Compound 103 (racemic mixture) was subjected to preparative HPLC SFC separation: Chiralpak IA (2×25 cm), 20% ethanol (0.1% DEA)/CO$_2$, 100 bar, 65 mL/min, 254 nm, inj vol.: 1 mL, 15 mg/mL, (1:1) methanol:DCM to give Compound 106 (single enantiomer present in the earlier eluting fraction) and Compound 107 (single enantiomer present in the late eluting fraction).

Compound 106 (98% ee): yellow solid, [α]p=−4.3 (c=1.00, MeOH), $^1$H NMR (CD$_3$OD, 600 MHz) δ: 7.32-7.36 (m, 2H), 7.27-7.31 (m, 2H), 3.89 (t, J=6.7 Hz, 1H), 3.02-3.05 (m, 1H), 1.60-1.72 (m, 1H), 1.28-1.31 (m, 3H), 1.20-1.27 (m, 2H), 0.92 (s, 3H), 0.90 (s, 3H).

Compound 107 (>99% ee): yellow solid, [α]$_D$=+4.2 (c=1.00, MeOH), $^1$H NMR (CD$_3$OD, 600 MHz) δ: 7.32-7.36 (m, 2H), 7.27-7.31 (m, 2H), 3.89 (t, J=6.7 Hz, 1H), 3.02-3.05 (m, 1H), 1.60-1.72 (m, 1H), 1.28-1.31 (m, 3H), 1.20-1.27 (m, 2H), 0.92 (s, 3H), 0.90 (s, 3H).

Biological Data

Biological activity of some specific compounds of the invention is set forth in Table 1 below. CHO-Gα16 cells stably expressing FPR1 or FPR2 were cultured in (Ham's F12 nutrient media, 10% fetal bovine serum, 1% PSA (penicillin, streptomycin, amphotericin B antiobiotic/antimycotic), 400 μg/ml geneticin and 50 μg/ml hygromycin). In general, the day before the experiment, 18,000 cells/well were plated in a 384-well clear bottom poly-D-lysine coated plate. The following day the screening compound-induced calcium activity was assayed on the FLIPR$^{Tetra}$. The drug plates were prepared in 384-well microplates using the EP3 and the MultiPROBE robotic liquid handling systems. Compounds were tested at concentrations ranging from 0.61 to 10,000 nM. Results are expressed as EC$_{50}$ (nM) and efficacy values.

TABLE 1

| Compound No. | Structure, properties | FPR2 Gα16-CHO EC$_{50}$ (% eff) | FPR1 Gα16-CHO EC$_{50}$ (% eff) | Ratio FPR2:FPR1 (EC$_{50}$) |
|---|---|---|---|---|
| 100 | earlier eluting racemate | 3765 nM (0.75) | 1421 nM (0.80) | 2.6 |
| 101 | later eluting racemate | 10k nM (0.73) | 10k nM (0.66) | 1 |
| 102 | racemate | 1053 nM (0.63) | 48 nM (0.92) | 22 |

TABLE 1-continued
| Compound No. | Structure, properties | FPR2 Gα16-CHO EC$_{50}$ (% eff) | FPR1 Gα16-CHO EC$_{50}$ (% eff) | Ratio FPR2:FPR1 (EC$_{50}$) |
|---|---|---|---|---|
| 103 | 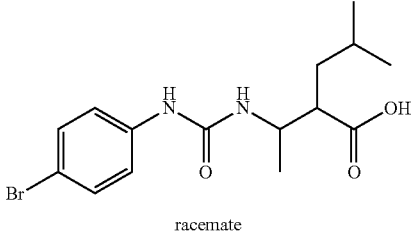 [SMILES: CC(C)CC(C(=O)O)C(C)NC(=O)Nc1ccc(Br)cc1]<br>racemate | 41 nM (1.04) | 0.52 nM (0.97) | 79 |
| 104 | 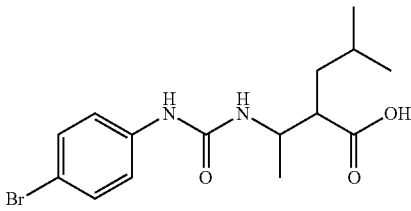<br>enantiomer [>99% ee, [α]$_D$ = +31.7 (c = 1.00, MeOH)] | 855 nM (0.89) | 51 nM (0.94) | 17 |
| 105 | 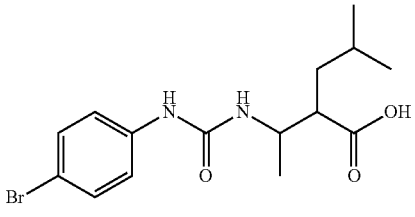<br>enantiomer [>99% ee, [α]$_D$ = -30.6 (c = 1.00, MeOH)] | 3239 nM (0.56) | 13 nM (1.03) | 249 |
| 106 | 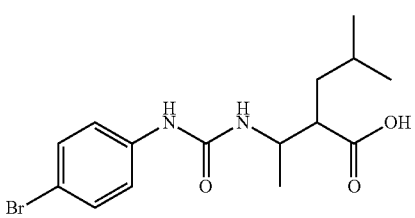<br>enantiomer [98% ee, [α]$_D$ = -4.3 (c = 1.00, MeOH)] | 9941 nM (0.75) | 98 nM (0.91) | 101 |
| 107 | 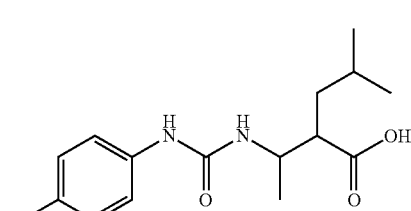<br>enantiomer [>99% ee, [α]$_D$ = +4.2 (c = 1.00, MeOH)] | 25 nM (0.96) | 1.7 nM (0.93) | 15 |

What is claimed:
1. A compound of Formula I:

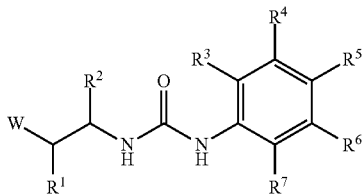

Formula I wherein:
W is —COOH;
R$^1$ is optionally substituted C$_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{14}$R$^{15}$, urea, —COOH, —C(O)OC$_{1-6}$ alkyl, —C(O)NH$_2$, optionally substituted C$_{3-8}$ cycloalkyl, optionally substituted C$_{3-8}$ cycloalkenyl, optionally substituted C$_{6-10}$ aryl, and optionally substituted heterocycle;
R$^2$ is optionally substituted C$_{1-6}$ alkyl, wherein said optional substituent is selected from the group consisting of —OH, —SH, —OC$_{1-6}$ alkyl, —SC$_{1-6}$ alkyl, —NH$_2$, —NH(C$_{1-6}$ alkyl), —NR$^{14}$R$^{15}$, urea, —COOH, —C(O)OC$_{1-6}$ alkyl, —C(O)NH$_2$, optionally substituted C$_{3-8}$ cycloalkyl, optionally substituted C$_{3-8}$ cycloalkenyl, optionally substituted C$_{6-10}$ aryl, and optionally substituted heterocycle;
R$^3$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^9$, —S(O)$_m$R$^{10}$, —C(O)R$^{11}$, —SR$^{12}$ or —OR$^{12}$;
R$^4$ is H, optionally substituted C$_{1-6}$ alkyl, C$_{1-6}$ haloalkyl, halogen, —S(O)$_m$R$^{10}$ or —C(O)R$^{11}$;
R$^5$ is optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —S(O)$_m$R$^{10}$, —C(O)R$^{11}$, —SR$^{13}$ or —OR$^{13}$;
R$^6$ is H, optionally substituted C$_{1-6}$ alkyl, C$_{1-6}$ haloalkyl, halogen, —S(O)$_m$R$^{10}$ or —C(O)R$^{11}$;
R$^7$ is H, optionally substituted C$_{1-6}$ alkyl, C$_{1-6}$ haloalkyl, optionally substituted C$_{3-8}$ cycloalkyl, optionally substituted C$_{3-8}$ cycloalkenyl, optionally substituted C$_{6-10}$ aryl, optionally substituted heterocycle, halogen, —NR$^8$R$^9$, —S(O)$_m$R$^{10}$, —C(O)R$^{11}$, —SR$^{12}$ or —OR$^{12}$;
R$^8$ is H, optionally substituted C$_{1-6}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^9$ is H, optionally substituted C$_{1-6}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^{10}$ is —OH, optionally substituted C$_{1-6}$ alkyl or optionally substituted C$_{6-10}$ aryl;
R$^{11}$ is —OH, optionally substituted C$_{1-6}$ alkyl or optionally substituted C$_{6-10}$ aryl;
R$^{12}$ is H or optionally substituted C$_{1-8}$ alkyl;
R$^{13}$ is H, optionally substituted C$_{1-8}$ alkyl, optionally substituted C$_{3-8}$ cycloalkyl, optionally substituted C$_{3-8}$ cycloalkenyl, optionally substituted C$_{6-10}$ aryl or optionally substituted heterocycle;
R$^{14}$ is C$_{1-6}$ alkyl;
R$^{15}$ is C$_{1-6}$ alkyl; and
each m is independently 1 or 2;
or a mixture of two or more diastereomers thereof;
or a mixture of enantiomers thereof;
or an individual enantiomer or diastereoisomer thereof;
or a pharmaceutically acceptable salt of any of the foregoing;
provided that the compound is not:

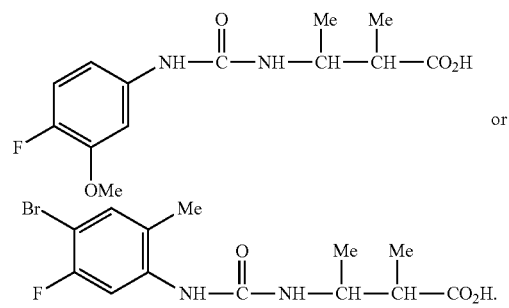

2. The compound of claim 1, wherein R$^1$ is optionally substituted C$_{2-6}$ alkyl.
3. The compound of claim 1, wherein:
W is —COOH;
R$^1$ is unsubstituted C$_{2-6}$ alkyl;
R$^2$ is methyl;
R$^3$ is H or F;
R$^4$ is H;
R$^5$ is CF$_3$, F, Cl or Br;
R$^6$ is H; and
R$^7$ is H or F.
4. The compound of claim 3, wherein R$^1$ is unsubstituted ethyl, n-propyl, isopropyl, n-butyl, sec-butyl, iso-butyl or tert-butyl.
5. The compound of claim 3, wherein:
R$^1$ is iso-butyl;
R$^3$ is H;
R$^5$ is Br;
R$^7$ is H.
6. The compound of claim 1, selected from the group consisting of:

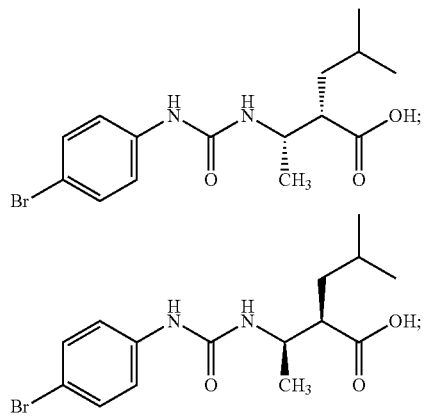

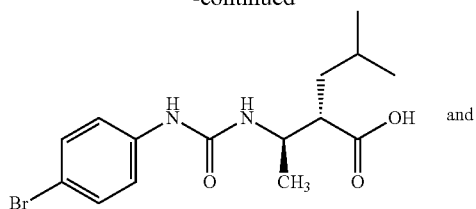 and
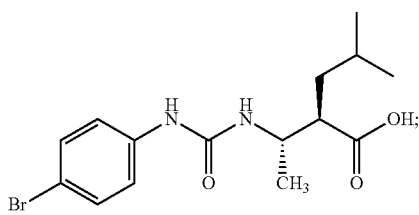
and a mixture of any two or more of the foregoing;
and pharmaceutically acceptable salts thereof.
7. A pharmaceutical composition comprising a therapeutically effective amount of a compound of claim 1, and a pharmaceutically acceptable excipient.
* * * * *